US009260529B2

(12) United States Patent
Hayden-Ledbetter et al.

(10) Patent No.: US 9,260,529 B2
(45) Date of Patent: Feb. 16, 2016

(54) MOLECULES THAT BIND CD180, COMPOSITIONS AND METHODS OF USE

(75) Inventors: Martha Hayden-Ledbetter, Shoreline, WA (US); Jeffrey Ledbetter, Shoreline, WA (US)

(73) Assignee: The University of Washington Through Its Center For Commercialization, Seattle, WA (US)

( * ) Notice: Subject to any disclaimer, the term of this patent is extended or adjusted under 35 U.S.C. 154(b) by 249 days.

(21) Appl. No.: 13/034,144

(22) Filed: Feb. 24, 2011

(65) Prior Publication Data

US 2012/0020965 A1    Jan. 26, 2012

Related U.S. Application Data

(60) Provisional application No. 61/307,801, filed on Feb. 24, 2010.

(51) Int. Cl.
| | |
|---|---|
| *C07K 16/28* | (2006.01) |
| *C12N 5/0781* | (2010.01) |
| *C07K 16/30* | (2006.01) |
| *A61K 39/395* | (2006.01) |

(52) U.S. Cl.
CPC .......... *C07K 16/2896* (2013.01); *C12N 5/0635* (2013.01); *A61K 39/39541* (2013.01); *A61K 39/39558* (2013.01); *C07K 16/28* (2013.01); *C07K 16/30* (2013.01); *C07K 2317/24* (2013.01); *C07K 2317/52* (2013.01); *C07K 2317/54* (2013.01); *C07K 2317/622* (2013.01); *C07K 2317/64* (2013.01); *C07K 2317/71* (2013.01); *C07K 2317/73* (2013.01); *C07K 2317/74* (2013.01); *C12N 2501/056* (2013.01); *C12N 2501/599* (2013.01)

(58) Field of Classification Search
CPC ................ A61K 2039/505; A61K 39/39541; A61K 39/39558; C07K 16/28; C07K 16/30
USPC ........... 530/350, 387.1, 387.3, 387.7, 388.22, 530/388.8
See application file for complete search history.

(56) References Cited

U.S. PATENT DOCUMENTS

| | | | |
|---|---|---|---|
| 4,946,778 A | 8/1990 | Ladner et al. | |
| 5,132,405 A | 7/1992 | Huston et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 7,297,775 B2 | 11/2007 | Idusogie et al. | |
| 7,317,091 B2 | 1/2008 | Lazar et al. | |
| 7,335,742 B2 | 2/2008 | Presta | |
| 7,371,826 B2 | 5/2008 | Presta | |
| 7,416,727 B2 | 8/2008 | Presta | |
| 7,662,925 B2 | 2/2010 | Lazar et al. | |
| 7,754,209 B2 * | 7/2010 | Ledbetter et al. .......... 424/133.1 |
| 2003/0118592 A1 | 6/2003 | Ledbetter et al. | |
| 2003/0133939 A1 | 7/2003 | Ledbetter et al. | |
| 2007/0111281 A1 | 5/2007 | Sondermann et al. | |
| 2007/0212733 A1 * | 9/2007 | Martin .......................... 435/7.21 |
| 2009/0214539 A1 * | 8/2009 | Grosmaire et al. ......... 424/135.1 |
| 2010/0279932 A1 * | 11/2010 | Ledbetter et al. ............. 514/7.3 |
| 2011/0003337 A1 | 1/2011 | Benhar et al. | |

FOREIGN PATENT DOCUMENTS

WO    2005/018572    3/2005

OTHER PUBLICATIONS

Miura et al. (Blood. Oct. 15, 1998; 92 (8): 2815-22).*
Ding et al. (J. Cell. Mol. Med. Jun. 2010; 14 (6B): 1717-25.*
Oganesyan et al. (Acta Crystallogr. D Biol. Crystallogr. Jun. 2008; 64 (Pt. 6):700-4).*
Porakishvili et al. (Br. J. Haematol. Nov. 2005; 131 (3): 313-9).*
Kenanova et al. (Cancer. Res. Jan. 15, 2005; 65 (2): 622-31).*
Olafsen et al. (Cancer Res. Jul. 1, 2005; 65 (13): 5907-16).*
Gottfried et al. (Immunobiology. 2003; 207 (5): 351-9).*
Roshak et al. (J. Leukoc. Biol. Jan. 1999; 65 (1):43-9).*
Nagai et al. (Blood. Mar. 1, 2002; 99 (5): 1699-705).*
Yamashita et al. (J. Exp. Med. Jul. 1, 1996; 184 (1): 113-20).*
Ogata et al. (J. Exp. Med. Jul. 3, 2000; 192 (1): 23-9).*
Chaplin et al. (J. Immunol. Oct. 15, 2011; 187 (8): 4199-209).*
Cao et al. (Appl. Biochem. Biotechnol. Jun. 2009; 157 (3): 562-74).*
Rudikoff et al (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Winkler et al. (J. Immunol. Oct. 15, 2000; 165 (8): 4505-4514).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Tawara et al. (J. Immunol. Feb. 15, 2008; 180 (4): 2294-8).*
Idusogie et al. (J. Immunol. 2000; 164: 4178-84).*
Thommesen et al. (Mol. Immunol. Nov. 2000; 37 (16): 995-1004).*
Taylor et al. (J. Leukoc. Biol. Sep. 2002; 72 (3): 522-9).*

(Continued)

*Primary Examiner* — Stephen Rawlings
(74) *Attorney, Agent, or Firm* — McDonnell Boehnen Hulbert & Berghoff LLP

(57) ABSTRACT

The present invention provides novel CD180 binding molecules, methods for their identification, and methods for their use.

1 Claim, 17 Drawing Sheets

(56) References Cited

OTHER PUBLICATIONS

Figure 1:
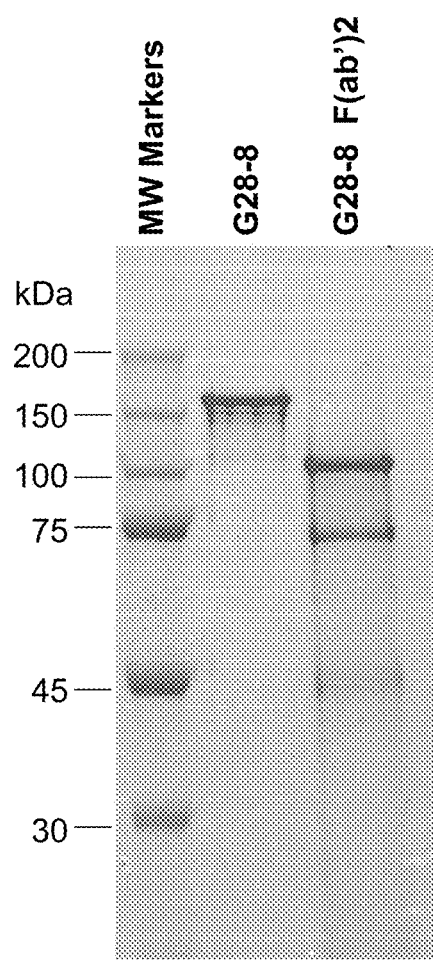

Presta LG, Biochemical Society Transactions 30 (part 4) 487-490 (2002).
Kostelny et al.. (1992) J Immunol 148:1547.
Gruber et al. (1994) J Immunol :5368.
Zhu et al. (1997) Protein Sci 6:781.
Hu et al. (1996) Cancer Res. 56:3055.
Adams et al. (1993) Cancer Res. 53:4026.
McCartney, et al. (1995) Protein Eng. 8:301.
Huse et al., Science 246:1275-1281 (1989).
Ward et al., Nature 341:544-546 (1989).
Vaughan et al., Nature Biotech. 14:309-314 (1996).
Jones et al., Nature 321:522-525 (1986).
Riechmann et al., Nature 332:323-329 (1988).
Presta, Curr. Op. Struct. Biol. 2:593-596 (1992).
Verhoeyen et al., Science 239:1534-1536 (1988).
Hoogenboom & Winter, J. Mol. Biol. 227:381 (1991).
Marks et al., J. Mol. Biol. 222:581 (1991).
Cole et al., Monoclonal Antibodies and Cancer Therapy, p. 77 (1985).
Boerner et al., J. Immunol. 147(1):86-95 (1991).
Marks et al., Bio/Technology 10:779-783 (1992).
Lonberg et al., Nature 368:856-859 (1994).
Morrison, Nature 368:812-13 (1994).
Fishwild et al., Nature Biotechnology 14:845-51 (1996).
Neuberger, Nature Biotechnology 14:826 (1996).
Lonberg & Huszar, Intern. Rev. Immunol. 13:65-93 (1995).
Huston et al., Proc. Nat'l Acad. Sci. USA 8:5879 (1988).
Bird et al., Science 242:4236 (1988).
Glockshuber et al., Biochemistry 29:1362 (1990).
Stemmer et al., Biotechniques 14:256-265 (1993).
Ehrhardt and Cooper, Curr. Top. Microbiol. Immunol, Aug. 3, 2010 (Immunoregulatory Roles for Fc Receptor-Like Molecules).
Davis et al., Ann. Rev. Immunol, 2007; 25:525-60 (Fc receptor-like molecules).
Swainson et al. J. Immunol. Apr. 2010 1:184(7):3639-47.
Parham. J Immunol. Dec. 1983;131(6):2895-902).
Lyons et al. J. Immunol. Methods, 171:131-137, 1994.
Valentine MA. J. Immunol. 1988; 140(12):4071-4078.
Miyake K, J Immunol. 1995; 154(7):3333-3340.
Divanovic S,. Nat. Immunol. 2005; 6(6):571-578.
Nagai Y. Blood 2002; 99(5):1699-1705.
Groeneveld PH. Immunobiology 1985; 170(5):402-411.
Fedele G. Microbes Infect. 2007; 9(7):855-863.
O'Neill La. Nat. Rev. Immunol. 2007; 7(5):353-364.
Jin MS. Cell 2007; 130(6):1071-1082.
Trinchieri G. Nat. Rev. Immunol. 2007; 7(3):179-190.
Zhu Q. Proc. Natl. Acad. Sci. USA 2008; 105(42):16260-16265.
Nagai Y. J. Immunol. 2005; 174(11):7043-7049.
Kim HM. Cell 2007; 130(5):906-917.
Tsuneyoshi, N. J. Immunol. 2005; 174(1):340-344.
Harada H J. Mol. Biol. 2010; 400(4):838-846.
Miyake K. J. Exp. Med. 1994; 180(4):1217-1224.
Chan VW. J. Exp. Med. 1998; 188(1):93-101.
Yazawa N. Blood 2003; 102(4):1374-1380.
Nunez Miguel R. PLoS One 2007; 2(8):e788.
Nyman T. J. Biol. Chem. 2008; 283(18):11861-11865.
Divanovic S. J. Leukoc. Biol. 2007; 82(2):265-271.
Chou TC. Adv. Enzyme Regul. 1984; 22:27-55.
Ogata H. J. Exp. Med. 2000; 192(1):23-29.
Goroff DK. J. Immunol. 1991; 146(1):18-25.
Finkelman F. J. Immunol. 1987; 138(9):2826-2830.
Finkelman F. J. Immunol. 1982; 129(2):629-637.
Finkelman F J. Immunol. 1982; 129(2):638-646.
Park SR. Eur. J. Immunol. 2005; 35(3):946-956.
Rijkers GT. Proc. Nat. Acad. Sci. USA. 1990; 87(22):8766-8770.
He B. Nat. Immunol. 2010; 11(9):836-845.
Eaton-Bassiri A. Infect. Immun. 2004; 72(12):7202-7211.
DiLillo DJ. Ann. N. Y. Acad. Sci. 2010; 1183:38-57.
Moore KW. Annu. Rev. Immunol. 2001; 19:683-765.
Rousset F. Proc. Natl. Acad. Sci. USA 1992; 89(5):1890-1893.

* cited by examiner

Schematic Structure of anti-CD180 scFv-Fc Molecules.

Figure 6.
Nucleotide and predicted amino acid sequence for G28-8 scFv-Fc

```
        HindIII      NcoI
        --------     ------
                        M  E    T  P  A    Q  L  L  F    L  L  L    L  W  L
  1     GTTAAGCTTG  CCACCATGGA  AACCCAGCG   CAGCTTCTCT   TCCTCCTGCT  ACTCTGGCTC
        CAATTCGAAC  GGTGGTACCT  TTGGGTCGC   GTCGAAGAGA   AGGAGGACGA  TGAGACCGAG
                    AgeI
                    ------
         P  D  T    T  G  D  I    Q  M  T    Q  S  P  A    S  L  S    A  S  V
  61    CCAGATACCA  CCGGTGACAT  CCAGATGACT  CAGTCTCCAG   CCTCCCTATC  TGCATCTGTG
        GGTCTATGGT  GGCCACTGTA  GGTCTACTGA  GTCAGAGGTC   GGAGGGATAG  ACGTAGACAC
         G  E  T    V  T  I  T    C  R  A    S  E  K  I    Y  S  Y    L  A  W
  121   GGAGAAACTG  TCACCATCAC  ATGTCGAGCA  AGTGAGAAGA   TTTACAGTTA  TTTAGCATGG
        CCTCTTTGAC  AGTGGTAGTG  TACAGCTCGT  TCACTCTTCT   AAATGTCAAT  AAATCGTACC
         Y  Q  Q    K  Q  G  K    S  P  Q    L  L  V  Y    N  A  K    T  L  A
  181   TATCAGCAGA  AACAGGGAAA  ATCTCCTCAG  CTCCTGGTCT   ATAACGCAAA  AACCTTAGCA
        ATAGTCGTCT  TTGTCCCTTT  TAGAGGAGTC  GAGGACCAGA   TATTGCGTTT  TTGGAATCGT
         E  G  V    P  S  R  F    S  V  S    G  S  G  T    Q  F  S    L  R  I
  241   GAAGGTGTGC  CATCAAGGTT  CAGTGTCAGT  GGATCAGGCA   CACAGTTTTC  TCTGAGGATC
        CTTCCACACG  GTAGTTCCAA  GTCACAGTCA  CCTAGTCCGT   GTGTCAAAAG  AGACTCCTAG
         N  S  L    Q  P  E  D    F  G  T    Y  Y  C  Q    N  N  F    G  S  P
  301   AACAGCCTGC  AGCCTGAAGA  TTTTGGGACT  TATTACTGTC   AACATAATTT  TGGTTCTCCT
        TTGTCGGACG  TCGGACTTCT  AAAACCCTGA  ATAATGACAG   TTGTATTAAA  ACCAAGAGGA
                                                        BglII
                                                        ------
         R  T  F    G  G  G  T    K  L  E    I  K  D  L    G  G  G    G  S  G
  361   CGGACGTTCG  GTGGAGGCAC  CAAACTGGAA  ATCAAAGATC   TGGGAGGAGG  TGGCTCAGGT
        GCCTGCAAGC  CACCTCCGTG  GTTTGACCTT  TAGTTTCTAG   ACCCTCCTCC  ACCGAGTCCA
                                                                    AgeI
                                                                    ------
         G  G  S    G  G  G    G  S  G    G  G  S    T  G  E    V  Q  L
  421   GGTGGAGGAT  CTGGAGGAGG  TGGAGTGGT   GGAGGTGGTT   CTACCGGTGA  GGTCCAGCTG
        CCACCTCCTA  GACCTCCTCC  ACCTCACCA   CCTCCACCAA   GATGGCCACT  CCAGGTCGAC
                                                                    EcoRV
                                                                    ------
         Q  Q  S    G  P  E  L    V  K  P    G  A  S  N    K  I  S    C  K  A
  481   CAACAGTCTG  GACCTGAACT  GGTGAAGCCT  GGAGCTTCAA   TGAAGATATC  CTGCAAGGCT
        GTTGTCAGAC  CTGGACTTGA  CCACTTCGGA  CCTCGAAGTT   ACTTCTATAG  GACGTTCCGA
                                                                    NcoI
                                                                    ------
         S  G  Y    S  F  T  G    Y  T  M    N  W  V  K    Q  S  H    G  K  T
  541   TCTGGTTACT  CATTCACTGG  CTACACCATG  AACTGGGTGA   AGCAGAGCCA  TGGAAAGACC
        AGACCAATGA  GTAAGTGACC  GATGTGGTAC  TTGACCCACT   TCGTCTCGGT  ACCTTTCTGG
         L  E  W    I  G  L  I    N  P  Y    N  G  V  T    S  Y  N    Q  K  F
  601   CTTGAATGGA  TTGGACTTAT  TAATCCTTAC  AATGGTGTTA   CTAGCTACAA  CCAGAAGTTC
        GAACTTACCT  AACCTGAATA  ATTAGGAATG  TTACCACAAT   GATCGATGTT  GGTCTTCAAG
         K  D  K    A  T  L  T    V  D  K    S  S  S  T    A  Y  M    E  L  L
  661   AAGGACAAGG  CCACATTAAC  TGTAGACAAG  TCATCCAGCA   CAGCCTACAT  GGAACTCCTC
        TTCCTGTTCC  GGTGTAATTG  ACATCTGTTC  AGTAGGTCGT   GTCGGATGTA  CCTTGAGGAG
```

Figure 6.
continued

```
            S  L  T  S  E  D  S     A  I  Y     Y  C  A  R     D  Y  N     Y  D  Y
721  AGTCTGACAT CTGAGGACTC TGCAATCTAT TACTGTGCAA GAGACTATAA TTACGACTAC
     TCAGACTGTA GACTCCTGAG ACGTTAGATA ATGACACGTT CTCTGATATT AATGCTGATG
                                                    BglII
                                                  ~~~~~~~
                                                         XhoI
                                                       ~~~~~~~
            F  D  Y  W     G  Q  G     T  T  L     T  V  S  S     D  L  E     P  K  S
781  TTTGACTACT GGGGCCAAGG CACCACTCTC ACAGTCTCCT GAGATCTCGA GCCCAAATCT
     AAACTGATGA CCCCGGTTCC GTGGTGAGAG TGTCAGAGGA CTCTAGAGCT CGGGTTTAGA
            S  D  K  T  H  T  C     P  P  C     P  A  P  E     L  L  G     G  S  S
841  TCTGACAAAA CTCACACATG TCCACCGTGT CCAGCACCTG AACTCCTGGG TGGATCGTCA
     AGACTGTTTT GAGTGTGTAC AGGTGGCACA GGTCGTGGAC TTGAGGACCC ACCTAGCAGT
            V  F  L  F     P  P  K     P  K  D     T  L  M  I     S  R  T     P  E  V
901  GTCTTCCTCT TCCCCCCAAA ACCCAAGGAC ACTCTCATGA TCTCCCGGAC CCCTGAGGTC
     CAGAAGGAGA AGGGGGGTTT TGGGTTCCTG TGAGAGTACT AGAGGGCCTG GGGACTCCAG
            T  C  V  V  V  D  V     S  Q  E     D  P  E  V     Q  F  N     W  Y  V
961  ACGTGCGTGG TGGTGGACGT GAGCCAGGAA GACCCCGAGG TCCAGTTCAA CTGGTACGTG
     TGCACGCACC ACCACCTGCA CTCGGTCCTT CTGGGGCTCC AGGTCAAGTT GACCATGCAC
            D  G  M  E  V  H  N     A  K  T     K  P  R  E     Q  F  N     S  T
1021 GACGGCATGG AGGTGCATAA TGCCAAGACA AAGCCACGGG AGGAGCAGTT CAACAGCACG
     CTGCCGTACC TCCACGTATT ACGGTTCTGT TTCGGTGCCC TCCTCGTCAA GTTGTCGTGC
            F  R  V  V  S  V  L     T  V  V     H  Q  D  W     L  N  G     K  E  Y
1081 TTCCGTGTGG TCAGCGTCCT CACCGTCGTG CACCAGGACT GGCTGAACGG CAAGGAGTAC
     AAGGCACACC AGTCGCAGGA GTGGCAGCAC GTGGTCCTGA CCGACTTGCC GTTCCTCATG
            K  C  K  V  S  N  K     A  L  P     A  S  I  E     K  T  I     S  K  T
1141 AAGTGCAAGG TCTCCAACAA AGCCCTCCCA GCCTCCATCG AGAAAACAAT CTCCAAAACC
     TTCACGTTCC AGAGGTTGTT TCGGGAGGGT CGGAGGTAGC TCTTTTGTTA GAGGTTTTGG
            K  G  Q  P  R  E  P     Q  V  Y     T  L  P  P     S  R  E     E  M  T
1201 AAAGGGCAGC CCCGAGAACC ACAGGTGTAC ACCCTGCCCC CATCCCGGGA GGAGATGACC
     TTTCCCGTCG GGGCTCTTGG TGTCCACATG TGGGACGGGG GTAGGGCCCT CCTCTACTGG
            K  N  Q  V  S  L  T     C  L  V     K  G  F  Y     P  S  D     I  A  V
1261 AAGAACCAGG TCAGCCTGAC CTGCCTGGTC AAAGGCTTCT ATCCCAGCGA CATCGCCGTG
     TTCTTGGTCC AGTCGGACTG GACGGACCAG TTTCCGAAGA TAGGGTCGCT GTAGCGGCAC
            E  W  E  S  N  G  Q     P  E  N     N  Y  N  T     T  P  P     V  L  D
1321 GAGTGGGAGA GCAATGGGCA GCCGGAGAAC AACTACAACA CCACGCCTCC CGTGCTGGAC
     CTCACCCTCT CGTTACCCGT CGGCCTCTTG TTGATGTTGT GGTGCGGAGG GCACGACCTG
            S  D  G  S  F  F  L     Y  S  K     L  T  V  D     K  S  R     W  Q  Q
1381 TCCGACGGCT CCTTCTTCCT CTACAGCAAG CTCACCGTGG ACAAGAGCAG GTGGCAGCAG
     AGGCTGCCGA GGAAGAAGGA GATGTCGTTC GAGTGGCACC TGTTCTCGTC CACCGTCGTC
            G  N  V  F  S  C  S     V  M  H     E  A  L  H     N  H  Y     T  Q  K
1441 GGGAACGTCT TCTCATGCTC CGTGATGCAT GAGGCTCTGC ACAACCACTA CACGCAGAAG
     CCCTTGCAGA AGAGTACGAG GCACTACGTA CTCCGAGACG TGTTGGTGAT GTGCGTCTTC
                                                           XbaI
                                                         ~~~~~~~
            S  L  S  L  S  P  G     K  *
1501 AGCCTCTCTC TGTCTCCGGG TAAATGATAA TCTAGA
     TCGGAGAGAG ACAGAGGCCC ATTTACTATT AGATCT
```

Binding of G28-8 scFv-Fc to Ramos B cells.

Figure 9A-B
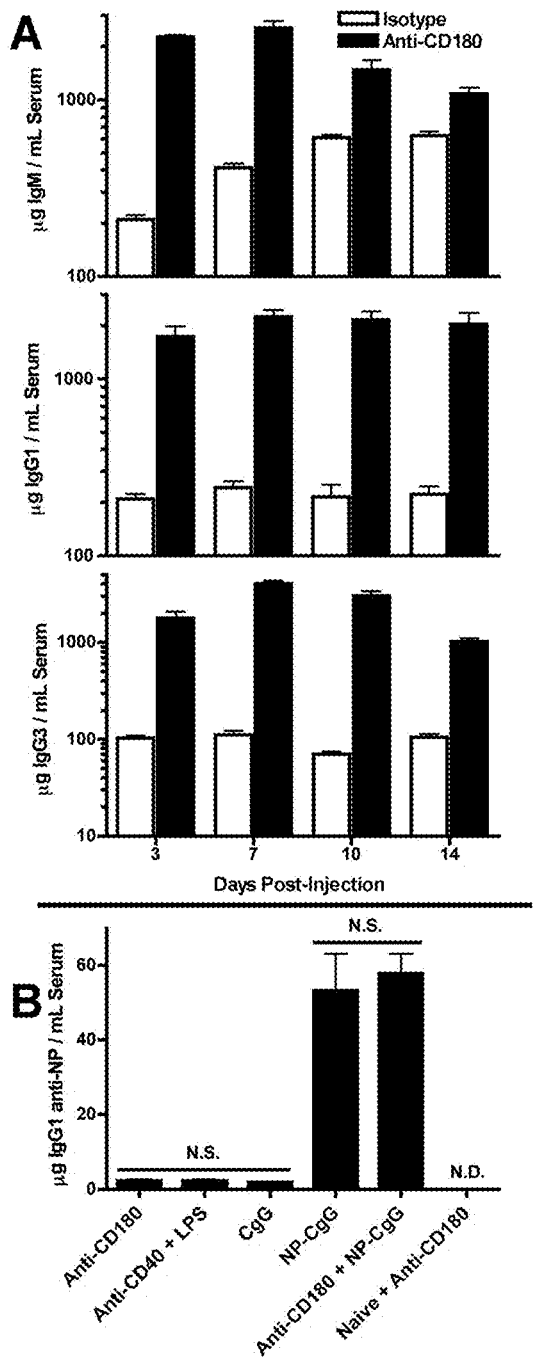

MOLECULES THAT BIND CD180, COMPOSITIONS AND METHODS OF USE

STATEMENT OF U.S. GOVERNMENT SUPPORT

This invention was made with U.S. government support under DE16381, AI44257, and AI85311 awarded by the National Institutes of Health. The U.S. Government has certain rights in the invention.

RELATED APPLICATIONS

This application claims prior to U.S. Provisional Patent Application Ser. No. 61/307,801 filed Feb. 24, 2010, which is incorporated by reference herein in its entirety.

TECHNICAL FIELD

The present disclosure relates to regulation of activation and function of antigen-presenting cells such as B cells, myeloid cells, and dendritic cells. The disclosure provides compositions that activate CD180 and methods for their use. The disclosure also provides a method for stimulation of polyclonal immunoglobulin production for potential therapeutic application by binding to the CD180 receptor on B cells.

BACKGROUND

Toll-like receptors (TLRs) are pattern recognition receptors that bind a variety of microbial products such as microbial membrane lipids or nucleic acids. Antigen presenting cells (APC) including B cells, DCs and macrophages express multiple TLRs that are bound by pathogens to activate NF-κB and MAP kinase pathways, resulting in expression of costimulatory molecules and cytokine secretion. While TLRs are important for defense against infectious disease, increasing evidence suggests that TLRs also function as regulators of immune responses in cancer, autoimmune disease, and transplantation.

CD180 is a toll-like receptor (TLR) with a short cytoplasmic tail, lacking the Toll IL-1 Receptor (TIR) domain that mediates signal transduction and that is shared by all other TLRs. CD180 has an extracellular structure analogous to TLR4, with 22 leucine rich repeats and an associated co-receptor, MD1, required for CD180 expression. CD180 is expressed at relatively high levels by B cells, and at lower levels by dendritic cells (DC) and other myeloid cells.

G28-8 was the first mAb made to CD180, and was found to stimulate proliferation of B cells and to activate rapid calcium mobilization. Antibodies that bind to CD180 in the mouse also cause B cell proliferation and induce MAP kinase activation, and the responses depend upon the expression of the protein tyrosine kinases lyn and btk. However, the mechanism of CD180 signal transduction is unknown since CD180 does not appear to signal directly through its short cytoplasmic tail.

CD180 is thought to be a regulator of TLR-4 responses. In CD180 deficient animals, B cell proliferation and antibody responses to TLR-4 stimulation by LPS were markedly reduced, whereas TNFα production and septic shock after LPS treatment were increased. Thus CD180 has been proposed to be a positive regulator of TLR-4 responses by B cells but a negative regulator of TLR-4 responses by myeloid cells and DCs. There have been no reported studies of the function of engineered CD180 binding domains.

SUMMARY

In a first aspect, the present invention provides isolated CD180 antibody or an antigen binding fragment thereof, wherein the antibody or antigen binding fragment thereof comprises a human CD180 binding domain linked to an immunoglobulin constant region (Fc) domain that has impaired binding to human Fc receptor FcγRIIb.

In a second aspect, the present invention provides isolated nucleic acids encoding the antibodies of the invention.

In a third aspect, the present invention provides recombinant expression vectors comprising the isolated nucleic acids of the invention.

In a fourth aspect, the present invention provides recombinant host cells comprising the recombinant expression vectors of the invention.

In a fifth aspect, the present invention provides methods for producing monoclonal immunoglobulin, comprising (a) culturing the host cells of the invention under conditions suitable for expression of the nucleic-acid encoded antibody; and (b) isolating the antibody from the cultured cells.

In a sixth aspect, the present invention provides methods for increasing serum immunoglobulin (Ig) level, comprising administering to a subject in need thereof an antibody against CD180, or antigen binding fragment thereof, wherein the antibody comprises a human CD180 binding domain and does not possess a functional Fc domain, wherein the antibody is administered in an amount effective to increase serum Ig level.

In a seventh aspect, the present invention provides methods for plasma protein replacement therapy, comprising administering to a subject in need thereof an antibody against CD180, or antigen binding fragment thereof, wherein the antibody comprises a human CD180 binding domain and does not possess a functional Fc domain, wherein the antibody is administered in an amount effective to maintain adequate antibody levels in the subject.

In an eighth aspect, the present invention provides methods for treating a disorder selected from the group consisting of an immune deficiency, hypogammaglobulinemia, hyper-IgM syndrome, autoimmune disease, cancer, graft rejection, and infections, comprising, administering to a subject in need thereof an amount of an antibody against CD180, or antigen binding fragment thereof, wherein the antibody comprises a human CD180 binding domain and does not possess a functional Fc domain, wherein the amount of antibody administered is effective to treat immune deficiency, hypogammaglobulinemia, autoimmune disease, cancer, graft rejection, and infections.

BRIEF DESCRIPTION OF THE DRAWINGS

FIG. 1 shows SDS-PAGE analysis of G28-8 whole antibody and F(ab')2.

FIG. 2 shows CFSE fluorescence intensity versus MHC class II (DR) brightness of human lymphocytes after incubation for 4 days with either medium alone, with mAb G28-8, or with F(ab')2 fragment of G28-8.

FIG. 3 shows a histogram of CFSE fluorescence intensity versus cell frequency gated on the DR positive population of human blood lymphocytes, comparing the unstimulated, G28-8 stimulated, and G28-8 F(ab')2 stimulated cells.

FIG. 4 shows a dose titration of G28-8 or G28-8 F(ab')2 in stimulation of human B cell proliferation, graphed as the percentage of DR positive lymphocytes proliferating after 4 days culture, calculated from FloJo software (Ashland, Oreg.).

Figure 5:
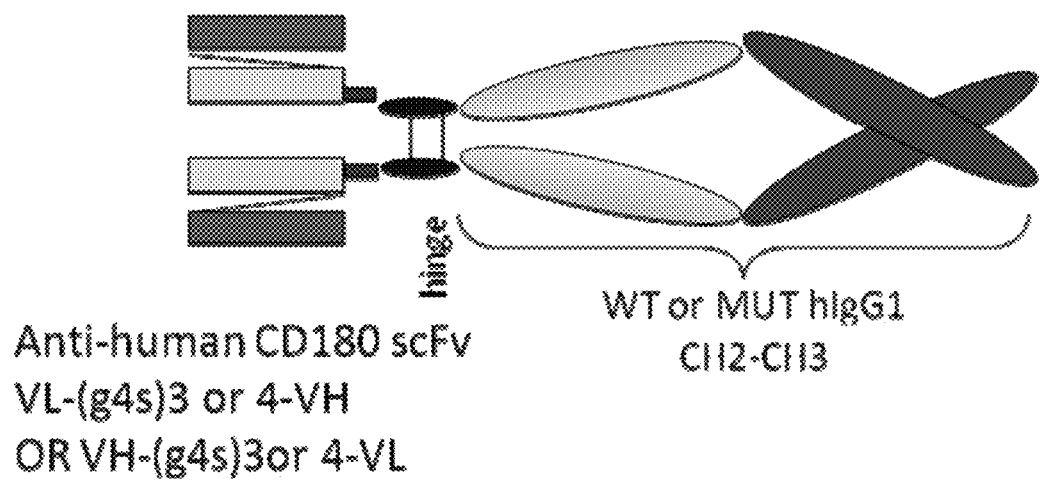

FIG. 5 shows a schematic diagram of the structure of the CD180 specific scFv-Fc.

FIG. 6 shows the nucleotide (SEQ ID NO:1) and predicted amino acid sequence (SEQ ID NO:2) of an exemplary antibody of the invention, a scFv-Fc molecule constructed from the cloned variable regions of mAb G28-8. The Fc domain of the recombinant molecules is an altered human IgG1 Fc domain with three amino acid changes (P238S, P331S, K322S) that reduce the binding of the molecule to Fc-receptors and C1q.

Figure 7:
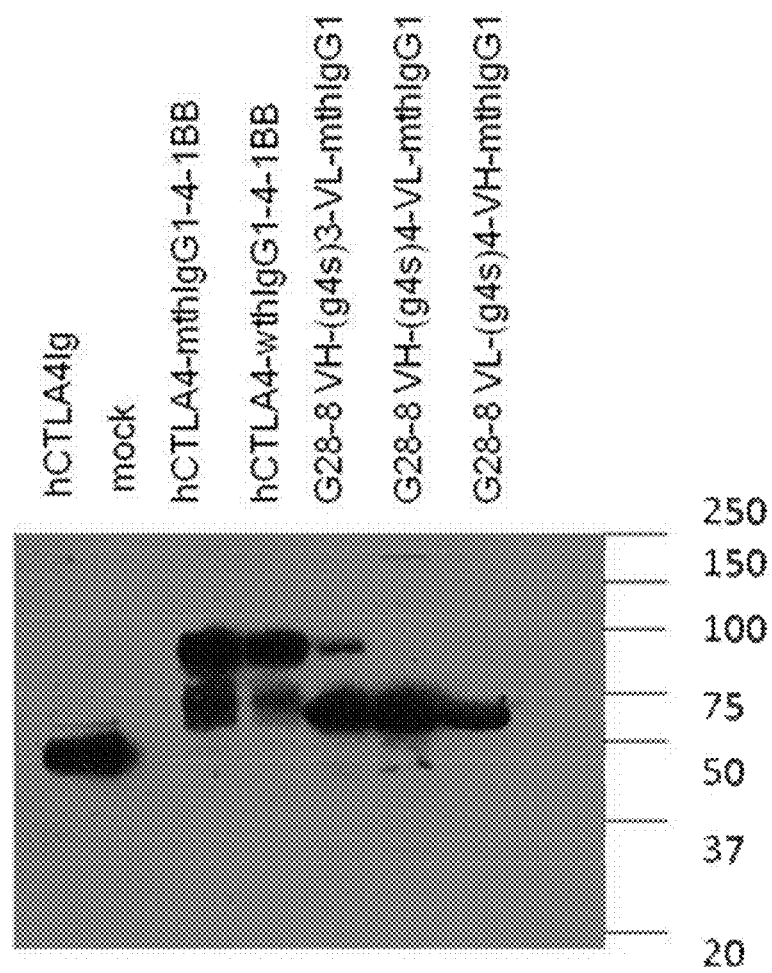

FIG. 7 shows a Western Blot of three different G28-8 scFvs along with CTLA4Ig, and CTLA4-Ig-4-1BB fusion proteins. Each molecule was immunoprecipitated with protein A agarose from 0.5 ml culture supernatants from COS7 cell transient transfections. COS7 cells were transiently transfected by polyfect reagent (QIAGEN) using 2.5 ug plasmid minipreps.

Figure 8:
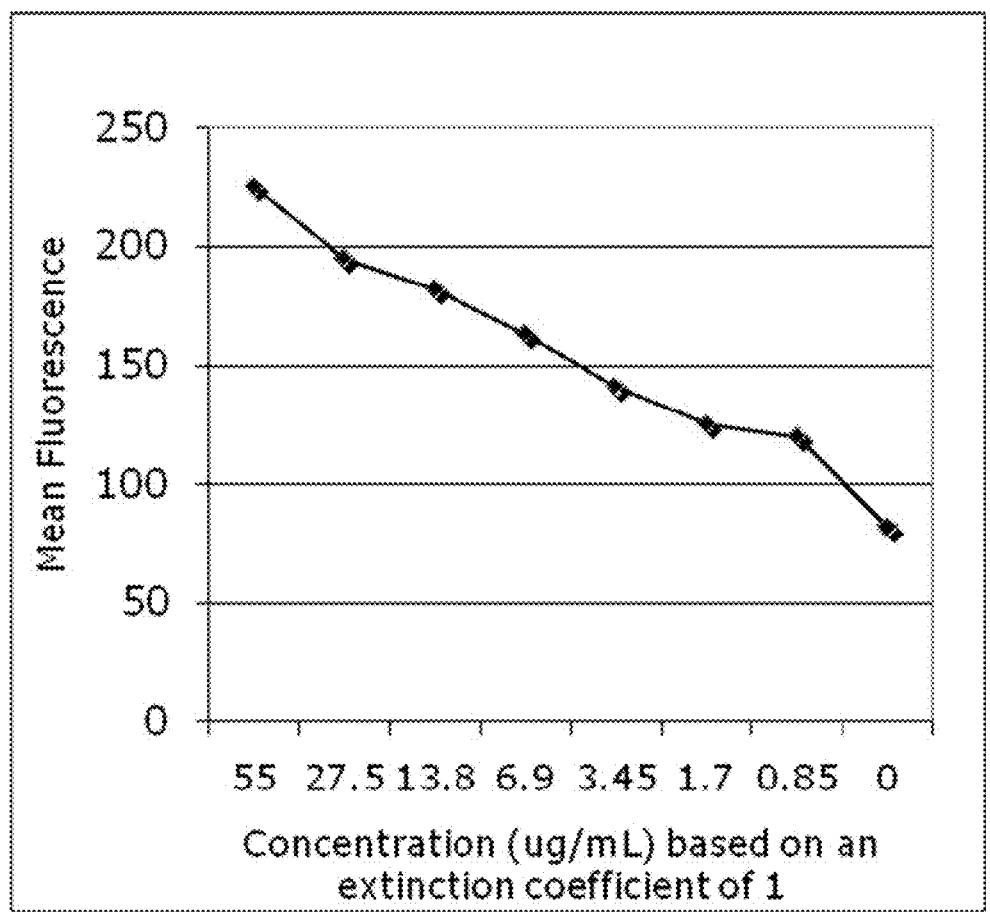

FIG. 8 shows the binding of one of the recombinant G28-8 scFv-Fc molecules to an immortalized human B cell line.

FIG. 9. Anti-CD180 rapidly induces Ig production independently of memory recall, T cell help, or MyD88 signals. A) WT mice received 250 µg anti-CD180 or isotype control mAb, bled at indicated timepoints, and total serum Ig analyzed by ELISA. B) WT mice were immunized with 50 µg NP-CgG in alum, rested, and challenged with either 250 µg anti-CD180, 100 µg anti-CD40 plus 10 µg LPS, 25 µg uncongugated CgG, 10 µg NP-CgG, or anti-CD180 plus NP-CgG, and bled at day 10 for NP-specific Ig analysis. Non-immunized mice for the naïve group were age matched. C) WT, TCR KO, and MyD88 KO mice were injected, bled at day 10, and total serum Ig analyzed. p value between paired columns <0.001 unless otherwise noted. n=4, replicates=4 for all experiments.

Figure 10:
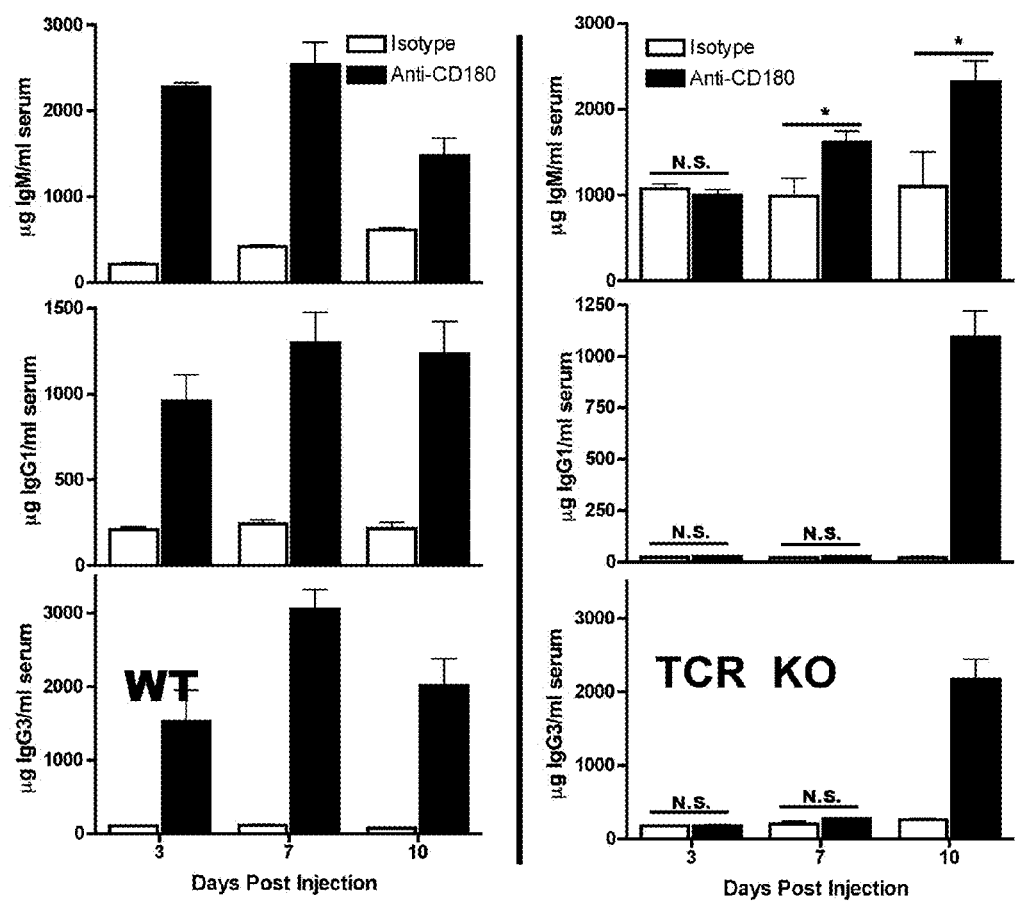

FIG. 10. T cell deficiency delays, but does not prevent, anti-CD180-induced Ig production. WT and TCR KO mice were injected with 250 µg anti-CD180 or isotype control mAb and total serum Ig analyzed by ELISA. p value between paired columns <0.001 unless otherwise noted. n=4, replicates=4.

Figure 11:
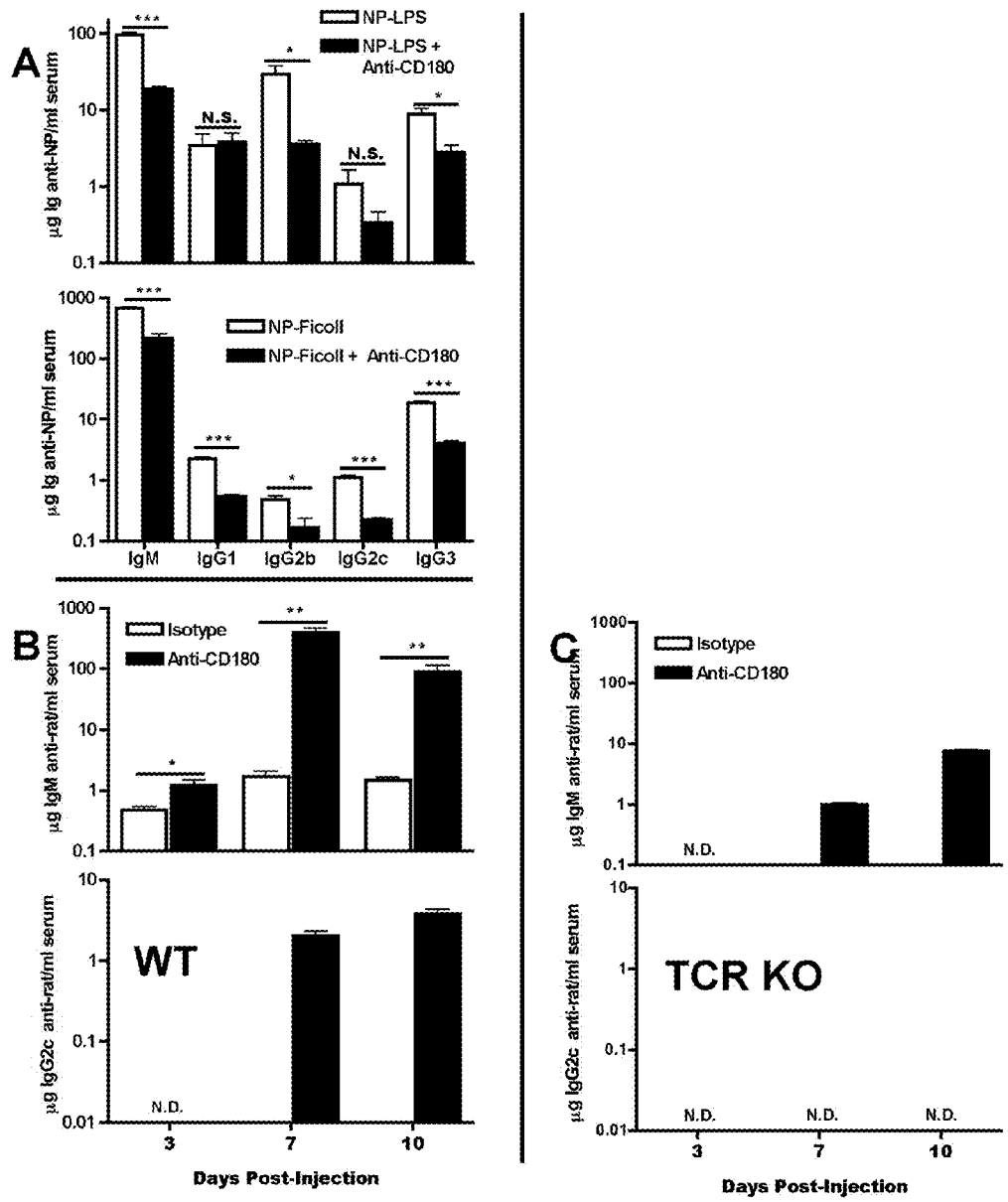

FIG. 11. T-Independent Type-1 and 2, but not T-Dependent antigen specific antibody, are decreased by co-administration of anti-CD180. A) WT mice were injected with 1 µg NP-LPS (0.7 NP/LPS) (TI-1), or 20 µg NP-Ficoll (152 NP/Ficoll) in combination with 250 µg anti-CD180 or isotype control mAb, bled on day 10, and serum analyzed for NP-specific antibody. B) WT and C) TCR KO mice were injected with 250 µg anti-CD180 or isotype control mAb, and serum analyzed for anti-rat Ig-specific IgM and IgG2c antibody from day three, seven, and 10 time points. p value between paired columns <0.001 unless otherwise noted. n=4, replicates=4 for all experiments.

Figure 12:
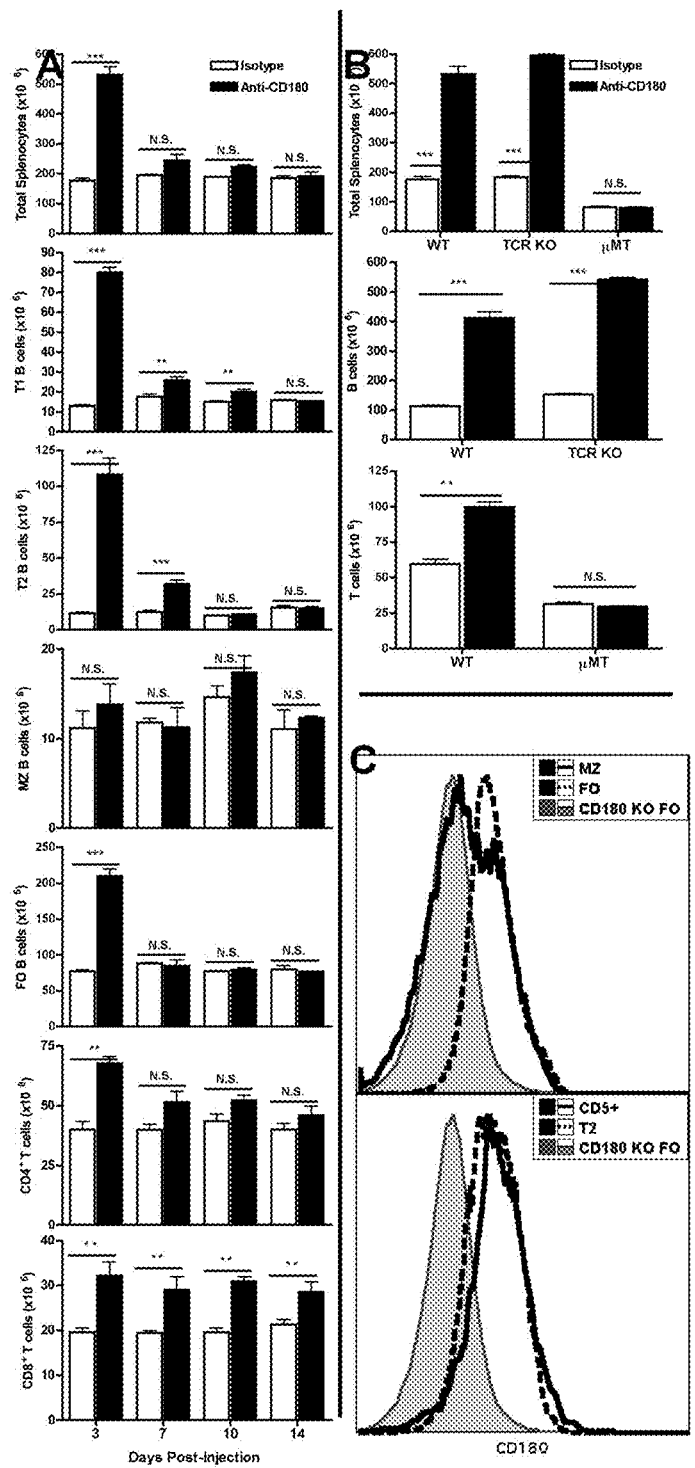

FIG. 12. Anti-CD180 injection expands and differentiates splenic B cells in vivo. A) Spleens were harvested and cells enumerated three, seven, 10, or 14 days following injection of 250 µg anti-CD180 or isotype mAb. Total splenocytes were subsetted by standard CD21/23/24 staining for B cell subsets and CD3/4/8β staining for T cell subsets. n=3, replicates=3. B) T cell-deficient (TCR KO) and B cell-deficient (µMT) mice were injected and splenocytes analyzed at the day three timepoint as in A. C) Unstimulated WT cells or those of a CD180 KO control were stained for CD180 expression and subsetted as in A.

Figure 13:
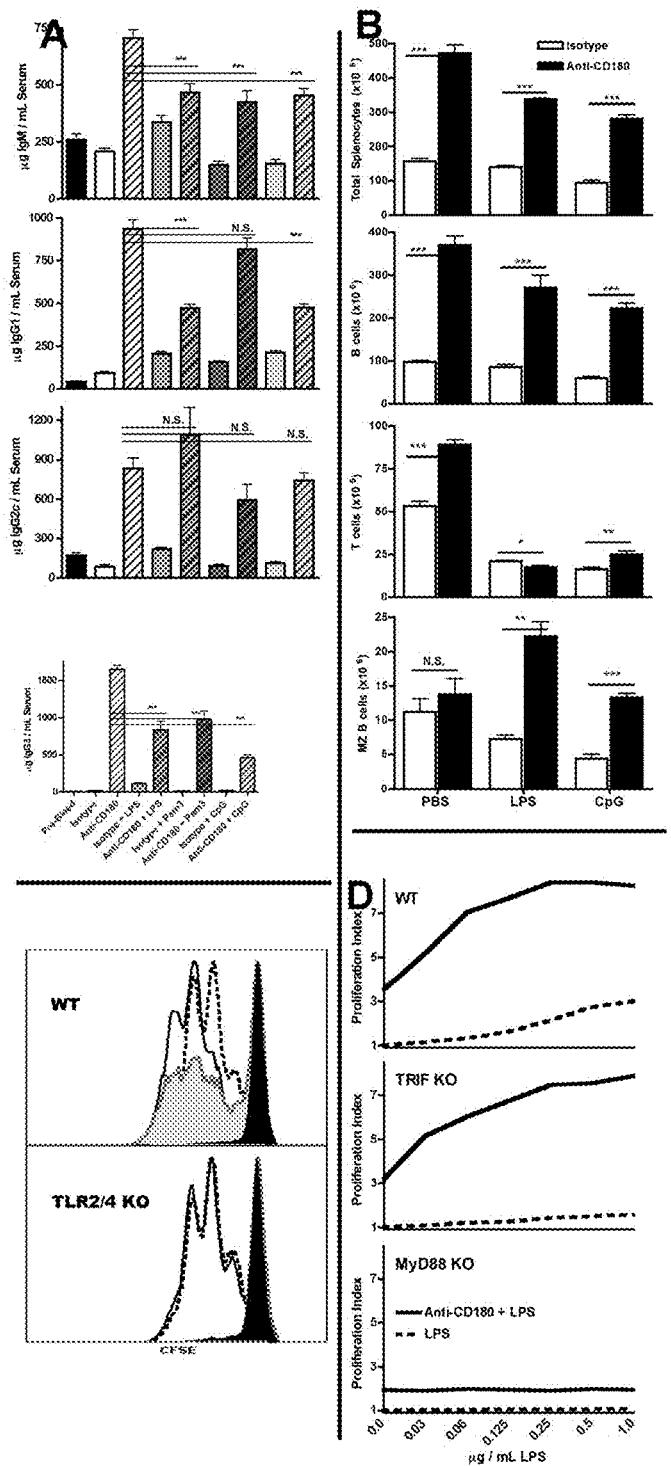

FIG. 13. TLR signals reduce anti-CD180 induced Ig production but augment proliferation in a MyD88-dependent manner. A) WT mice were injected with the following TLR agonists in combination with either 250 µg anti-CD180 or isotype control mAb: 1 µg LPS, 2 µg $Pam_3CSK_4$, or 10 µg CpG. Sera were obtained at day ten and analyzed by ELISA. n=4, replicates=3. B) TLR ligands LPS (10 µg), CpG (25 µg), or an equivalent volume of PBS were co-injected with either anti-CD180 or isotype and splenocytes were analyzed at the day 3 timepoint as above. n=3, replicates=3. C) CFSE labeled splenocytes from TLR2/4 KO or WT mice were cultured with anti-CD180 (0.2 µg/ml, dashed line), LPS (0.5 µg/ml, grey fill), or both (solid line), with an unstimulated control (black fill). B cells were gated (FSC/SSC, $B220^+$) and CFSE dilution analyzed. D) CFSE labeled splenocytes from WT, TRIF KO, or MyD88 KO mice were cultured with graded doses of LPS alone or in combination with a constant 0.1 µg/ml dose of anti-CD180. Proliferation Index is graphed against the corresponding LPS concentration. n=1, replicates=3.

Figure 14:
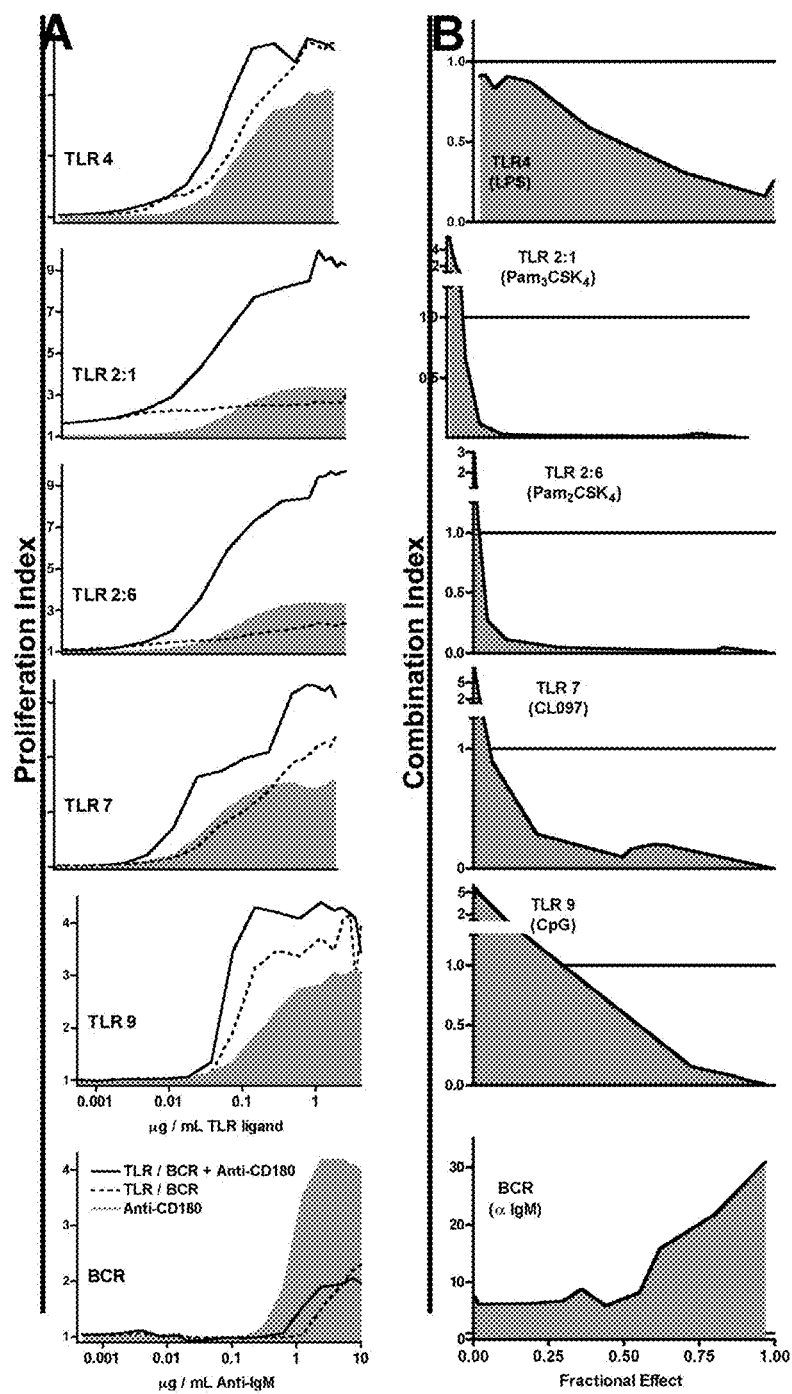

FIG. 14. Anti-CD180 synergizes for proliferation with all TLR ligands that signal through MyD88. A) Purified WT splenic B cells were stimulated with either TLR agonist alone, anti-CD180 alone, or both in constant ratio combinations. Proliferation Index was calculated for each series and all curves graphed against the corresponding TLR agonist concentrations. B) The three Proliferation Index curves were transformed into a single Combination Index (CI) curve as described in "Materials and methods". Combination Index values of 1 (reference bar) indicate simple additive effect (no interaction), CI values<1 indicate synergy (greater than additive effect), and CI values>1 indicate antagonism/inhibition. n=1, replicates=3.

Figure 15:
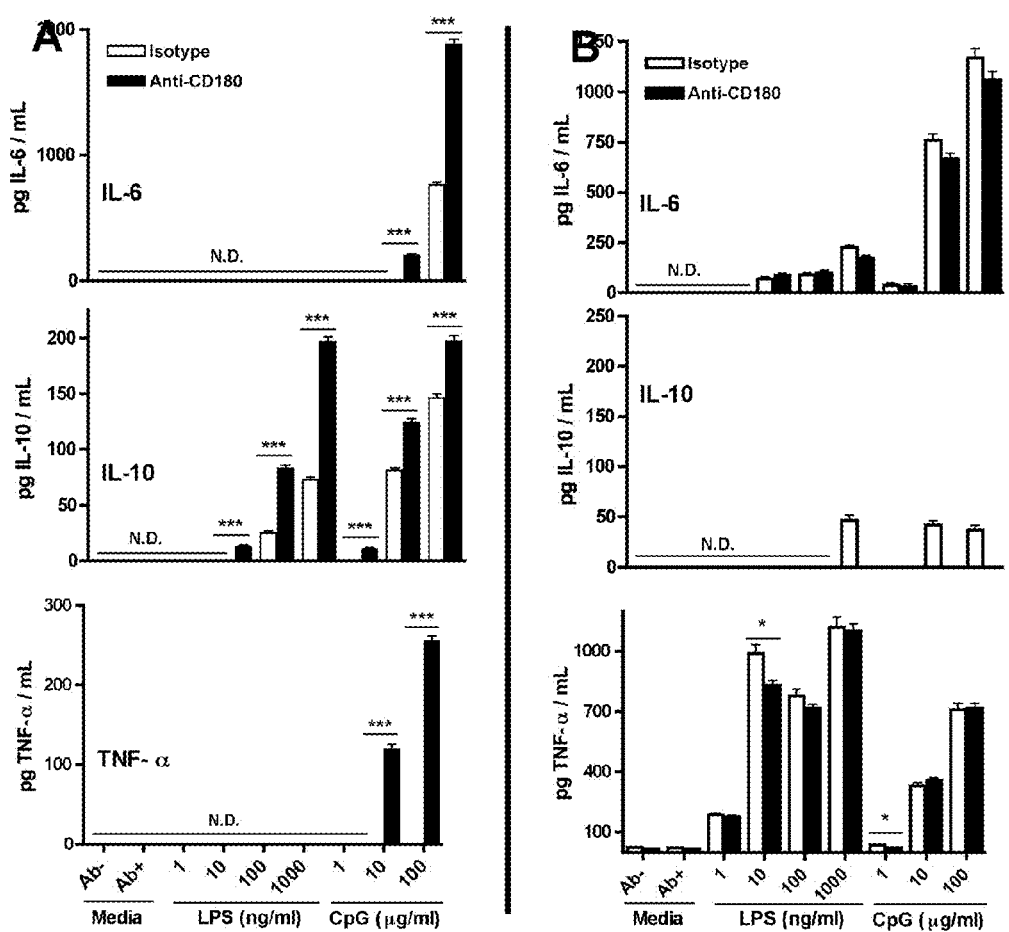

FIG. 15. Anti-CD180 does not induce cytokine production by B cells but augments induction by TLRs. A) Purified WT splenic B cells were seeded at $1 \times 10^6$ cells/ml in media with indicated stimulants. Overnight (24 hour) culture supernatants were assayed by ELISA. B) Purified WT splenic DCs were treated as in A. Differences between paired columns are not significant unless otherwise noted. n=3, replicates=2.

DETAILED DESCRIPTION

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number, respectively. Additionally, the words "herein," "above," and "below" and words of similar import, when used in this application, shall refer to this application as a whole and not to any particular portions of this application. As used herein, the singular forms "a", "an" and "the" include plural referents unless the context clearly dictates otherwise. "And" as used herein is interchangeably used with "or" unless expressly stated otherwise.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments.

All of the references cited herein are incorporated by reference. Aspects of the disclosure can be modified, if necessary, to employ the compositions, functions and concepts of the above references and application to provide yet further embodiments of the disclosure. These and other changes can be made to the disclosure in light of the detailed description.

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

In a first aspect, the present invention provides isolated CD180 antibody or an antigen binding fragment thereof, wherein the antibody or antigen binding fragment thereof comprises a human CD180 binding domain linked to an immunoglobulin constant region (Fc) domain that has impaired binding to human Fc receptor FcγRIIb.

The inventors have discovered that CD180 activation by antibody binding is inhibited by the antibody Fc domain's binding to the Fc receptor FcγRIIb. Thus, for example, a F(ab')2 fragment of anti-CD180 mAb G28-8, specific for human CD180, was significantly more potent than the intact antibody in stimulation of proliferation of human peripheral blood B cells. The inventors have further discovered that stimulation of CD180 in vivo causes a large increase in serum immunoglobulin levels with no requirement for co-administration of adjuvants or TLR agonists. This antibody production capability of the antibodies of the invention is completely unexpected. Serum immunoglobulin is important for protection from infection with bacteria, viruses, and parasites, and thus the antibodies and other therapeutics disclosed herein find application for the limiting and/or treating a wide variety of infections. Immunosuppressed patients, including patients with cancer undergoing chemotherapy or bone marrow transplantation often have low immunoglobulin levels and are treated with immunoglobulin preparations called IVIg, which is also approved for use in patients with autoimmune disease. Current methods for IVIg manufacturing use pooled serum from large numbers of donors (>10,000/batch). Thus, the antibodies and other therapeutics of the present invention represent a significant improvement over current IVIg therapies, since CD180 stimulation causes endogenous B cells to differentiate and produce antibody, thus reducing the potential for contamination with infectious agents and eliminating the need for infusions of large quantities of exogenous antibody. The antibodies of the invention can be produced in mammalian cell lines, such as CHO cells, without requiring the addition of serum, and can also be expected to significantly reduce the cost of IVIg-equivalent treatment.

The antibodies of the invention specifically bind to human CD180. The phrase "specifically (or selectively) bind" to human CD180 or "specifically (or selectively) immunoreactive with," human CD180, refers to a binding reaction that is determinative of the presence of CD180, in a heterogeneous population of proteins and other biologics. Thus, under designated immunoassay conditions, the antibodies bind to human CD180 at least two times the background and more typically more than 10 to 100 times background. Specific binding to an antibody under such conditions requires an antibody that is selected for its specificity for a particular protein. For example, polyclonal antibodies raised to human CD180, polymorphic variants, alleles, orthologs, and conservatively modified variants, or splice variants, or portions thereof, can be selected to obtain only those antibodies that are specifically immunoreactive with human CD180 protein and not with other proteins. This selection may be achieved, for example, by subtracting out antibodies that cross-react with other molecules. A variety of immunoassay formats may be used to select antibodies specifically immunoreactive with human CD180. For example, solid-phase ELISA immunoassays are routinely used to select antibodies specifically immunoreactive with a protein (see, e.g., Harlow & Lane, *Antibodies: A Laboratory Manual* (1988) and Harlow & Lane, *Using Antibodies* (1999) for a description of immunoassay formats and conditions that can be used to determine specific immunoreactivity).

In one embodiment, the antibodies of the invention compete with the monoclonal G28.8 antibody, or an antigen binding fragment thereof for binding to human CD180. The G28-8 antibody is a well characterized mouse IgG1 monoclonal anti-CD180 antibody that is commercially available from a variety of sources (Santa Cruz Biotechnology, Inc. (CA); BD Biosciences (CA); etc.) As is well known to those of skill in the art, a variety of competition assays can be used to assess competition of the antibodies or other compounds of the invention with mAb G28.8, for binding to human CD180. In one embodiment, competition also can be assessed by a flow cytometry test. For example, human CD180, or antigenic fragment thereof) can be incubated first with mAb G28.8, and then with an antibody (or other therapeutic compound) of the present invention labeled with a detectable label (such as a fluorophore or biotin). The test antibody typically is said to compete with the reference mAb G28.8 if the binding obtained after pre-incubation with saturating amount of the mAb G28.8 is about 80% or less, such as about 70% or less, about 60% or less, about 50% or less, about 40% or less, about 30% or less, about 20% or less, or about 10% or less, than the binding obtained by the test antibody without pre-incubation with mAb G28.8. As will be clear to those of skill in the art, the same assay could be conducted by pre-incubating with an antibody of the invention, and then labeling mAb G28.8 and carrying out the competition. Other competition assays are also well within the level of skill in the art, based on the teachings herein.

Binding affinity of the antibodies of the invention for human CD 180 is typically measured or determined by standard antibody-antigen assays, such as BIACORE™ competitive assays, saturation assays, or immunoassays such as enzyme-linked immunosorbent assay (ELISA) or radioimmunoassay (RIA). Such assays can be used to determine the dissociation constant of the antibody. The phrase "dissociation constant" refers to the affinity of an antibody for an antigen. Specificity of binding between an antibody and an antigen exists if the dissociation constant ($K_D$=1/K, where K is the affinity constant) of the antibody is <1 µM, preferably <100 nM, and most preferably <0.1 nM.

The antibodies of the invention have impaired binding to human immunoglobulin constant region Fc receptor FcγRIIb. The Fc domain in an antibody is composed of two heavy chains and is involved in selective binding to Fc receptors (FcR) on target cells. Surprisingly, the inventors have discovered that CD180 activation by anti-CD180 antibody binding is inhibited by the antibody Fc domain. As used herein, the antibodies have "impaired binding to human immunoglobulin constant region Fc receptor FcγRIIb" if binding of the Fc domain to the inhibitory Fc Receptor FcγRIIb is reduced by at least 50% relative to mAb G28.8 Fc domain binding to FcγRIIb. Methods for quantitating FcR binding have been described in the art. For example, see Presta L G, "Engineering therapeutic antibodies for improved function" Biochemical Society Transactions 30 (part 4) 487-490 (2002), U.S. Pat. Nos. 7,317,091; 7,662,925; 7,297,775, 7,371,826; 7,335,742; and 7,416,727, each incorporated by reference herein in their entirety. In various embodiments, "impaired binding" means binding of the Fc domain to the inhibitory Fc Receptor FcγRIIb is reduced by at least 60%, 70%, 80%, 90%, 100%, 200%, or more relative to mAb G28.8 Fc domain binding to FcγRIIb.

As used herein, "antibody" includes reference to an immunoglobulin molecule immunologically reactive with human CD180, and includes monoclonal antibodies. Various isotypes of antibodies exist, for example IgG1, IgG2, IgG3, IgG4, and other Ig, e.g., IgM, IgA, IgE isotypes. The term also includes genetically engineered forms such as chimeric antibodies (e.g., humanized murine antibodies) and heteroconjugate antibodies (e.g., bispecific antibodies), and fully humanized antibodies. As used throughout the application, the term "antibody" includes fragments with antigen-binding capability (e.g., Fab', F(ab')$_2$, Fab, Fv and rIgG. See also, Pierce Catalog and Handbook, 1994-1995 (Pierce Chemical Co., Rockford, Ill.). See also, e.g., Kuby, J., *Immunology*, 3$^{rd}$ Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol:* 5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301. Various antigen binding domain-fusion proteins are also disclosed, e.g., in US patent application Nos. 2003/0118592 and 2003/0133939, and are encompassed within the term "antibody" as used in this application.

An antibody immunologically reactive with human CD180 can be generated by recombinant methods such as selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

In one embodiment, the antibodies of the invention lack an Fc domain altogether. Exemplary such antibodies include, but are not limited to a Fab antibody, a Fab' antibody, a (Fab')$_2$ antibody, and an Fv antibody. In other embodiments, the antibodies of the invention possess an Fc domain that has impaired binding to human immunoglobulin constant region Fc receptor FcγRIIb domain, whether through truncation or mutation, as described herein. Such antibodies may be, for example, recombinant IgG, and an scFv-Fc antibodies.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs". The extent of the framework regions and CDRs has been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a V$_H$ CDR3 is located in the variable domain of the heavy chain of the antibody in which it is found, whereas a V$_L$ CDR1 is the CDR1 from the variable domain of the light chain of the antibody in which it is found.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

References to "V$_H$" or a "VH" refer to the variable region of an immunoglobulin heavy chain of an antibody, including the heavy chain of an Fv, scFv, or Fab. References to "V$_L$" or a "VL" refer to the variable region of an immunoglobulin light chain, including the light chain of an Fv, scFv, dsFv or Fab. In one embodiment, the antibody or an antigen binding fragment of the present invention has one or more CDRs from mAb G28.8 (ie: 1, 2, or 3 of V$_H$ CDR1, V$_H$ CDR2, and V$_H$ CDR3, and/or 1, 2, or 3 of V$_L$ CDR1, V$_L$ CDR2, and V$_L$ CDR3.

The antibodies of the invention may be single chain Fv ("scFv") antibodies. The phrase "single chain Fv" or "scFv" refers to an antibody in which the variable domains of the heavy chain and of the light chain of a traditional antibody have been joined to form one chain. Typically, one or more linker peptides is inserted between the chains to allow for proper folding and creation of an active binding site.

The antibodies of the invention may be chimeric antibodies. A "chimeric antibody" is an immunoglobulin molecule in which the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.

The antibodies of the invention may be humanized antibodies. A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mAb G28.8 (as described herein). In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody can also comprise at least a portion of an immunoglobulin constant region (Fc), typically that of a human immunoglobulin (Jones et al., *Nature* 321:522-525 (1986); Riechmann et al., *Nature* 332:323-329 (1988); and Presta, *Curr. Op. Struct. Biol.* 2:593-596 (1992)). Humanization can be essentially performed following the method of Winter and co-workers (Jones et al., *Nature* 321:522-525 (1986); Riechmann et al., *Nature* 332:323-327 (1988); Verhoeyen et al., *Science* 239: 1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

The antibodies of the invention can also be human antibodies, which can be produced using various techniques known in the art, including phage display libraries (Hoogenboom & Winter, *J. Mol. Biol.* 227:381 (1991); Marks et al., *J. Mol. Biol.* 222:581 (1991)). Other techniques are also available for the preparation of human monoclonal antibodies (Cole et al., *Monoclonal Antibodies and Cancer Therapy*, p. 77 (1985) and Boerner et al., *J. Immunol.* 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569, 825; 5,625,126; 5,633,425; 5,661,016, and in the following scientific publications: Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); Lonberg & Huszar, *Intern. Rev. Immunol.* 13:65-93 (1995).

In some embodiments, the antibody of the invention is a single chain Fv (scFv). The $V_H$ and the $V_L$ regions of a scFv antibody comprise a single chain which is folded to create an antigen binding site similar to that found in four chain antibodies. Once folded, noncovalent interactions stabilize the single chain antibody. While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston et al., *Proc. Nat'l Acad. Sci. USA* 8:5879 (1988); Bird et al., *Science* 242:4236 (1988); Glockshuber et al., *Biochemistry* 29:1362 (1990); U.S. Pat. No. 4,946,778, U.S. Pat. No. 5,132,405 and Stemmer et al., *Biotechniques* 14:256-265 (1993). Generally the peptide linker will have no specific biological activity other than to join the regions or to preserve some minimum distance or other spatial relationship between the $V_H$ and $V_L$. However, the constituent amino acids of the peptide linker may be selected to influence some property of the molecule such as the folding, net charge, or hydrophobicity. Single chain Fv (scFv) antibodies optionally include a peptide linker. Methods of making scFv antibodies have been described. See, Huse et al., supra; Ward et al. supra; and Vaughan et al., supra.

In some embodiments, the antibodies are bispecific (or multi-specific) antibodies. Bispecific antibodies are monoclonal, preferably human or humanized, antibodies that have binding specificities for at least one other antigen besides CD180 or that have binding specificities for different CD180 epitopes. In one embodiment, the isolated antibody or an antigen binding fragment comprises one or more Fc domain mutations to impair binding to the FcγRIIb receptor. Any suitable Fc domain mutants can be used so that the resulting Fc domain binding to the FcγRIIb receptor is reduced by at least 50% relative to mAb G28-8 Fc domain binding to the FcγRIIb receptor. Fc mutations and truncations that can be made to reduce binding of the antibodies of the invention to the FcγRIIb receptor can be made by those of skill in the art, based on the teachings herein, using binding assays to test for binding of the resulting antibodies to the FcγRIIb receptor as described herein and as are known in the art.

In one embodiment, the antibody is a human IgG4 mAb with human or humanized variable regions. In another embodiment, the antibody has an Fc domain of a human antibody with a mutation in the CH2 region so that the molecule is not glycosylated, including but not limited to N297 (EU numbering for human IgG heavy chain constant region) in SEQ ID NO:6. In another embodiment, the Fc domain is human IgG1 with the three cysteines of the hinge region (C220, C226, C229 in SEQ ID NO:6) each changed to serine, and the proline at position 238 of the CH2 domain changed to serine, and the proline at position 331 changed to serine. In another preferred embodiment, the Fc domain is human IgG1 with N297 in SEQ ID NO:6 changed to any other amino acid. In another embodiment, the Fc domain is human IgG1 with one or more amino acid change between positions 292 and 300 in SEQ ID NO:6. In another embodiment, the Fc domain is human IgG1 with an amino acid addition or deletion at any position between residues 292 and 300 in SEQ ID NO:6. In another embodiment, the Fc domain is human IgG1 with an SCC hinge; in a further embodiment an SSS hinge. In further embodiments, the Fc domain is human IgG1 with an SCC hinge and P238S/P331S mutations; with an SCC hinge and P238S/K322S/P331S mutations; an SSS hinge and P238S/P331S mutations; or an SSS hinge and P238S/K322S/P331S mutations. In another embodiment, the Fc domain is human IgG1 with mutations that alter binding by Fc gamma receptors (I, II, III) without affecting FcRn binding important for half life. In further embodiments Fc domain is as disclosed in Ehrhardt and Cooper, Curr. Top. Microbiol. Immunol, 2010 Aug. 3 (Immunoregulatory Roles for Fc Receptor-Like Molecules); Davis et al., Ann. Rev. Immunol, 2007; 25:525-60 (Fc receptor-like molecules); and Swainson et al., J. Immunol. 2010 Apr. 1: 184(7):3639-47.

In certain embodiments, antibodies of the invention comprise an amino acid substitution to an Fc domain which alters the antigen-independent effector functions of the antibody, in particular the circulating half-life of the antibody. Such antibodies exhibit either increased or decreased binding to FcRn when compared to antibodies lacking these substitutions and, therefore, have an increased or decreased half-life in serum, respectively. Fc variants with improved affinity for FcRn are anticipated to have longer serum half-lives, and such antibodies have useful applications in methods of treating mammals where long half-life of the administered antibody is desired. In contrast, Fc variants with decreased FcRn binding affinity are expected to have shorter half-lives, and such antibodies are also useful, for example, for administration to a mammal where a shortened circulation time may be advantageous, e.g. where the starting antibody has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the antibodies of the invention exhibit reduced transport across the epithelium of kidney glomeruli from the vasculature. In another embodiment, the antibodies of the invention exhibit reduced transport across the blood brain barrier (BBB) from the brain, into the vascular space. In one embodiment, a hybrid nuclease antibody with altered FcRn binding comprises at least one Fc domain (e.g., one or two Fc domains) having one or more amino acid substitutions within the "FcRn binding loop" of an Fc domain. Exemplary amino acid substitutions which altered FcRn binding activity are disclosed in International PCT Publication No. WO05/047327 which is incorporated by reference herein.

In other embodiments, an antibody of the invention comprises an Fc variant comprising an amino acid substitution which alters the antigen-dependent effector functions of the polypeptide, in particular ADCC or complement activation, e.g., as compared to a wild type Fc region. In exemplary embodiment, said antibodies exhibit altered binding to an Fc gamma receptor (e.g., CD16). Such antibodies exhibit either increased or decreased binding to FcR gamma when compared to wild-type polypeptides and, therefore, mediate enhanced or reduced effector function, respectively. Fc variants with improved affinity for FcγRs are anticipated to enhance effector function, and such antibodies have useful applications in methods of treating mammals where target molecule destruction is desired. In contrast, Fc variants with decreased FcγR binding affinity are expected to reduce effector function, and such antibodies are also useful, for example, for treatment of conditions in which target cell destruction is undesirable, e.g., where normal cells may express target molecules, or where chronic administration of the antibody might result in unwanted immune system activation. In one embodiment, the antibody comprising an Fc exhibits at least one altered antigen-dependent effector function selected from the group consisting of opsonization, phagocytosis, complement dependent cytotoxicity, antigen-dependent cellular cytotoxicity (ADCC), or effector cell modulation as compared to a polypeptide comprising a wild type Fc region.

In one embodiment the antibody exhibits altered binding to an activating FcγR (e.g. FcγI, FcγIIa, or FcγRIIIa). In another embodiment, the antibody exhibits altered binding affinity to an inhibitory FcγR (e.g. FcγRIIb). Exemplary amino acid substitutions which altered FcR or complement binding activity are disclosed in International PCT Publication No. WO05/063815 which is incorporated by reference herein.

An antibody of the invention may also comprise an amino acid substitution which alters the glycosylation of the CD180 binding molecule. For example, the Fc domain of the antibody may comprise an Fc domain having a mutation leading to reduced glycosylation (e.g., N- or O-linked glycosylation) or may comprise an altered glycoform of the wild-type Fc domain (e.g., a low fucose or fucose-free glycan). In another embodiment, the antibody has an amino acid substitution near or within a glycosylation motif, for example, an N-linked glycosylation motif that contains the amino acid sequence NXT or NXS. Exemplary amino acid substitutions which reduce or alter glycosylation are disclosed in International PCT Publication No. WO05/018572 and US Patent Publication No. 2007/0111281, which are incorporated by reference herein.

In a further embodiment, the Fc domain is a human IgG1 Fc domain comprising amino acid changes in one or more of P238S, P331S, and K322S (including but not limited to P238S/P331S, K322S, and combinations thereof). In this embodiment, it is further preferred that the antibody is an scFv-Fc antibody, and it is further preferred that the antibody comprises an amino acid sequence according to SEQ ID NO:2. As disclosed herein, the inventors have shown that such antibodies are significantly more potent that intact antibody (with functional Fc domain) in stimulation of proliferation of human peripheral blood B cells and production of serum immunoglobulin in mice.

As will be understood by those of skill in the art, in the antibodies of any embodiment or combination of embodiments disclosed herein, insertions/linkers can be inserted between functional domains. In one non-limiting embodiment, one or more linkers can be inserted between VL-VH or VH-VL; for example, ((gly4ser)3 and (gly4ser)4 insertions after the KLEIK (SEQ ID NO:9) sequence of the VL and before the beginning of VH—in this case EVQ—or after the LTVSS (SEQ ID NO:10) of the VH and before the DIQ of the VL—depending on the orientation of the V regions) Linkers could also be inserted after the scFv and before the hinge or other domains in more complex molecules. These could be gly-ser type linkers or other linkers, depending on the desired functional or spacing properties required. Other linkers could be inserted after the CH3 domain (PGK in human IgG1, to link the rest of a multispecific molecule to another binding moiety, such as another scFv)

In another embodiment, a polypeptide linker comprises or consists of a gly-ser linker. As used herein, the term "gly-ser linker" refers to a peptide that consists of glycine and serine residues. An exemplary gly/ser linker comprises an amino acid sequence of the formula (Gly$_4$Ser)n, wherein n is a positive integer (e.g., 1, 2, 3, 4, or 5). A preferred gly/ser linker is (Gly$_4$Ser)4. Another preferred gly/ser linker is (Gly$_4$Ser)3. Another preferred gly/ser linker is (Gly$_4$Ser)5. In certain embodiments, the gly-ser linker may be inserted between two other sequences of the polypeptide linker (e.g., any of the polypeptide linker sequences described herein). In other embodiments, a gly-ser linker is attached at one or both ends of another sequence of the polypeptide linker (e.g., any of the polypeptide linker sequences described herein). In yet other embodiments, two or more gly-ser linker are incorporated in series in a polypeptide linker. In one embodiment, a polypeptide linker of the invention comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule) and a series of gly/ser amino acid residues (e.g., a gly/ser linker such as (Gly$_4$Ser)n).

In another embodiment, a polypeptide linker of the invention comprises a non-naturally occurring immunoglobulin hinge region domain, e.g., a hinge region domain that is not naturally found in the polypeptide comprising the hinge region domain and/or a hinge region domain that has been altered so that it differs in amino acid sequence from a naturally occurring immunoglobulin hinge region domain. In one embodiment, mutations can be made to hinge region domains to make a polypeptide linker of the invention. In one embodiment, a polypeptide linker of the invention comprises a hinge domain which does not comprise a naturally occurring number of cysteines, i.e., the polypeptide linker comprises either fewer cysteines or a greater number of cysteines than a naturally occurring hinge molecule.

It will be understood by those of skill in the art that these various embodiments of the Fc mutations can be combined in the antibodies of the invention, unless the context clearly indicates otherwise. Similarly, it will be understood by those of skill in the art that these various embodiments of the Fc mutations can be mutations to the Fc domain of mAb G28.8, unless the context clearly indicates otherwise.

The antibodies of the invention may comprise conservative amino acid substitutions. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles consistent with the disclosure. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The antibodies of the invention may comprise one or more amino acid residues that are artificial chemical mimetic of a corresponding naturally occurring amino acid, as well as to naturally occurring amino acid polymers, those containing modified residues, and non-naturally occurring amino acid polymer. The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

The antibodies of any embodiment of the invention can further be conjugated to an effector moiety. The effector moiety can be any number of molecules, including labeling moieties such as radioactive labels or fluorescent labels, a TLR ligand or binding domain, or can be a therapeutic moiety. If the effector moiety is a therapeutic moiety, it will typically be a cytotoxic agent. In this method, targeting the cytotoxic agent to cancer cells, results in direct killing of the target cell. Cytotoxic agents are numerous and varied and include, but are not limited to, cytotoxic drugs or toxins or active fragments of such toxins. Suitable toxins and their corresponding fragments include RNase, diphtheria A chain, exotoxin A chain, ricin A chain, abrin A chain, curcin, crotin, phenomycin, enomycin, auristatin and the like. Cytotoxic agents also include radiochemicals made by conjugating radioisotopes to antibodies of the invention, or binding of a radionuclide to a chelating agent that has been attached to the antibody.

In another embodiment, the antibodies of the invention are modified to extend half-life, such as by attaching at least one molecule to the antibody for extending serum half life, including but not limited to a polyethlyene glycol (PEG) group, serum albumin, transferrin, transferrin receptor or the transferrin-binding portion thereof, or combinations thereof. As used herein, the word "attached" refers to a covalently or noncovalently conjugated substance. The conjugation may be by genetic engineering or by chemical means.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is isolated. In particular, an isolated nucleic acid is separated from some open reading frames that naturally flank the gene and encode proteins other than protein encoded by the gene. The term "isolated" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. In this sense, purification does not require that the purified compound be homogenous, e.g., 100% pure.

In another embodiment, the antibodies of the invention are present in a pharmaceutical formulation. In this embodiment, the antibodies, or pharmaceutically acceptable salts thereof, are combined with a pharmaceutically acceptable carrier. Suitable acids which are capable of forming such salts include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like. Suitable bases capable of forming such salts include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanol-amines (e.g., ethanolamine, diethanolamine and the like).

The pharmaceutical compositions of the invention may be made up in any suitable formulation, preferably in formulations suitable for administration by injection. In one embodiment, between about 50 and about 500 mg of antibody are present in about 1 to about 2 ml of the formulation; preferably between about 100 mg and about 250 mg in about 1 to about 2 ml of the formulation. In these embodiments, the antibody or antigen binding fragment thereof are present in about 25 mg/ml to about 500 mg/ml; in further embodiments, at between about 50 mg/ml and 250 mg/ml. Such pharmaceutical compositions can be used, for example, in the methods of the invention for increasing serum Ig levels or for plasma protein replacement therapy. The compositions of the invention are a dramatic improvement over current methods, which involve lengthy IV infusions of large amounts (150 grams or more) of suspended antibody.

In a second aspect, the present invention provides isolated nucleic acids encoding an antibody according to any embodiment of the present invention. The isolated nucleic acid sequence may comprise RNA or DNA. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. In one preferred embodiment, the isolated nucleic acid encodes a polypeptide with an amino acid sequence according to SEQ ID NO:2. In another embodiment, the isolated nucleic acid comprises or consists of the nucleic acid of SEQ ID NO:1, or a mRNA product thereof. The isolated nucleic acid sequences may further comprise conservatively modified variants of these nucleotide sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

In a third aspect, the present invention provides recombinant expression vectors comprising the isolated nucleic acids of the invention. The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes disclosed herein. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes disclosed herein. Similarly, a "recombinant protein" is a protein made using recombinant techniques, i.e., through the expression of a recombinant nucleic acid as depicted above.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

"Recombinant expression vector" includes vectors that operatively link a nucleic acid coding region or gene to any promoter capable of effecting expression of the gene product. The promoter sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In a fourth aspect, the present invention provides recombinant host cells comprising the recombinant expression vectors of the invention. The host cells can be either prokaryotic or eukaryotic. The cells can be transiently or stably transfected. Such transfection of expression vectors into prokaryotic and eukaryotic cells (including but not limited to Chinese hamster ovary (CHO) cells) can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (R. I. Freshney. 1987. Liss, Inc. New York, N.Y.).

In a fifth aspect, the present invention provides methods for method for producing immunoglobulin, comprising (a) culturing the host cells of the invention under conditions suitable for expression of the nucleic-acid encoded antibody; and (b) isolating the antibody from the cultured cells. In this embodiment, any embodiment of the host cells of the invention can be used. In one embodiment, prokaryotic host cells are used and the serum Ig is produced by methods known in the art, including but not limited that disclosed in US Published Patent Application 20110003337. In another embodiment, mammalian host cells are used, and standard culture conditions and isolation techniques are used.

Serum immunoglobulin is important for protection from infection with bacteria, viruses, and parasites, and thus the antibodies and other therapeutics disclosed herein find application for the limiting and/or treating a wide variety of infections. Immunosuppressed patients, including patients with cancer undergoing chemotherapy or bone marrow transplantation often have low immunoglobulin levels and are treated with immunoglobulin preparations called IVIg, which is also approved for use in patients with autoimmune disease. Current methods for IVIg manufacturing use pooled serum from large numbers of donors (>10,000/batch), thus increasing risk of infection, and requires infusion of 150+ grams of purified antibody over a two hour span. Thus, the methods of this aspect of the present invention represent a significant improvement over current IVIg production techniques, in that much smaller amounts of antibody can be administered intramuscularly or intravenuously, which stimulate the subject's B cells to produce large amounts of serum antibody and greatly reduces the risk of infection.

In a sixth aspect, the present invention provides methods for increasing serum immunoglobulin (Ig) level, comprising administering to a subject in need thereof an antibody against CD180, or antigen binding fragment thereof, wherein the antibody does not possess a functional Fc domain, wherein the antibody is administered in an amount effective to increase serum Ig level.

In a seventh aspect, the present invention provides methods for plasma protein replacement therapy, comprising administering to a subject in need thereof an antibody against CD180, or antigen binding fragment thereof, wherein the antibody does not possess a functional Fc domain, wherein the antibody is administered in an amount effective to maintain adequate antibody levels in the subject.

In the methods of the invention, the antibodies "do not possess a functional Fc domain," meaning that the Fc domain has impaired binding to immunoglobulin constant region Fc receptor FcγRIIb, as described herein. Thus, antibodies for use in the methods of the invention can be any of those disclosed herein, including antibodies that lack an Fc domain, and those in which the Fc domain is mutated or truncated to impair binding to FcγRIIb.

Most immunoglobulin present in the blood is natural antibody that contains germ-line variable regions without extensive somatic mutation. The natural antibody has reactivity towards multiple pathogens including bacteria and viruses, and is important in first-line defense and protection from infection. Natural antibodies mediate direct neutralization of bacteria or viruses present in the circulation and protect mice from encephalitis induced by vesicular stomatitis virus (VSV). In addition, natural antibodies have protective activity against intravenous infection with *S. pneumonia*. Natural antibodies also contribute to protection by enhancing phagocytosis of parasites. Results obtained in mice deficient in secreted IgM demonstrated a protective role for natural antibodies in bacterial clearance from the peritoneal cavity via activation of the complement cascade and the formation of the lytic complex, and also in the protection against a mucosal influenza infection. Natural antibodies provide an important link between innate and adaptive immunity by binding complement components in immune complexes, thus enhancing the uptake of antigen by complement receptors. Administration of the antibodies and other therapeutic molecules disclosed herein to subjects (e.g., humans, other non-human mammals) will increase levels of antibodies similar to natural antibody and should thus provide protection and enhanced immunity to a broad range of viruses, parasites, and bacteria. CD180 stimulation with embodiments of antibodies and other therapeutic molecules disclosed herein should enhance innate protection from multiple environmental toxins and infectious agents.

The sixth and seventh aspects of the invention can be used with any subject that can benefit from increased Ig levels and/or plasma protein replacement therapy. In a preferred embodiment, the subject's immune system is dysregulated (ie: overactive or deficient) due to a disorder, disease, or treatment including but not limited to subjects with IgG deficiencies, hypogammaglobulinemia, other immune deficiencies, undergoing chemotherapy or radiation therapy (ex: cancer patients, bone marrow transplantation patients, etc.), infections (bacterial, viral, parasite), autoimmune diseases, and hyper IgM syndrome.

In an eighth aspect, the present invention provides methods for treating a disorder selected from the group consisting of an immune deficiency, hypogammaglobulinemia, autoimmune disease, cancer, graft rejection, and infections, comprising, administering to a subject in need thereof an amount of an antibody against CD180, or antigen binding fragment thereof, wherein the antibody does not possess a functional Fc domain, wherein the amount of antibody administered is effective to treat immune deficiency, hypogammaglobulinemia, autoimmune disease, cancer, graft rejection, or infection. In addition to the methods disclosed above, the antibodies and other therapeutic molecules described herein are also useful for therapy of patients with autoimmune disease, cancer, or with dysregulated immune systems. As used herein, "treat" or "treating" means accomplishing one or more of the following: (a) reducing the severity of the disorder; (b) limiting or preventing development of symptoms characteristic of the disorder(s) being treated (ex: immune deficiencies in cancer patients (or other patients) undergoing chemotherapy and/or radiation therapy); (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

In each of the sixth, seventh, and eighth aspects of the invention, the antibody to be administered can be according to any embodiment or combination of embodiments of the antibodies disclosed herein. Thus, in one embodiment of any of these aspects, the antibody or antigen binding fragment thereof is the antibody or antigen binding fragment is selected from the group consisting of a Fab antibody, a Fab' antibody, a (Fab')$_2$ antibody, a rIg, and an scFv-Fc antibody. In another embodiment, the antibody or an antigen binding fragment has one or more complementarity-determining regions from mAb G28.8. In a further embodiment, the antibody comprises one or more Fc domain mutations to impair binding the CD180. In a still further embodiment, the Fc domain is a human IgG1 Fc domain comprising amino acid changes P238S, P331S, and K322S. In another embodiment, the antibody is an scFv-Fc antibody. In yet another embodiment, the antibody comprises an amino acid sequence according to SEQ ID NO:2. In any of these embodiments, the antibodies can be modified to extend half-life, such as by attaching at least one molecule to the antibody for extending serum half life, including but not limited to a polyethlyene glycol (PEG) group, serum albumin, transferrin, transferrin receptor or the transferrin-binding portion thereof, or combinations thereof.

Any suitable subject capable of immunoglobulin production can be treated according to the methods of the invention, including but not limited to humans, primates, dogs, cats, cattle, etc. The antibody to be used would (a) be specific for a CD180 of the subject to be treated (ie: human CD180 specific for human subjects, etc.), and (b) have a non-functional Fc domain that has impaired binding to FcγRIIb of the subject to be treated.

As used herein for all of the methods of the invention, an "amount effective" of the one or more antibodies or other therapeutics is an amount that is sufficient to provide the intended benefit of treatment. An effective amount of the antibodies or other therapeutics that can be employed ranges generally between about 0.01 µg/kg body weight and about 10 mg/kg body weight, preferably ranging between about 0.05 µg/kg and about 5 mg/kg body weight. However dosage levels are based on a variety of factors, including the type of injury, the age, weight, sex, medical condition of the individual, the severity of the condition, the route of administration, and the particular compound employed. In one embodiment, between about 50 and about 500 mg of antibody are administered IM or IV in about a 1 ml to about a 2 ml formulation; preferably between about 100 mg and about 250 mg in about a 1 ml to about a 2 ml formulation. Frequency of administration can also be determined by an attending physician in light of all appropriate factors. In exemplary embodiments, administration is one-two time per day, every other day, one-two times per week, once per month, once every other month, etc.

For administration, the antibodies or other therapeutics are ordinarily combined with one or more excipients appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, dextran sulfate, heparin-containing gels, and/or polyvinyl alcohol, and tableted or encapsulated for conventional administration. Alternatively, the antibodies or other therapeutics may be dissolved in saline, water, polyethylene glycol, propylene glycol, carboxymethyl cellulose colloidal solutions, and/or various buffers. The antibodies may be linked to other compounds to promote an increased half-life in vivo, such as described herein. Such linkage can be covalent or noncovalent as is understood by those of skill in the art.

The antibodies or other therapeutics may be administered by any suitable route, preferably intravenous or intramuscular administration.

In a ninth aspect, the present invention provides methods for identifying candidate immunostimulatory compounds comprising identifying molecules that (a) bind to and stimulate CD180, and B) have minimal binding (less than that of a normal antibody) to the inhibitory Fc receptor FcγRIIb on B cells. CD180 binding can be measured with any sort of capture assay, such as cell based flow cytometry assays or capture to an ELISA plate coated with purified soluble CD180 protein and then detected with an anti-Ig second step. Modifications to Fc domains to reduce binding to Fc receptors are disclosed herein and are known in the art. End activity of the constructs versus parent wild type antibodies (such as G28-8) can be carried out using any suitable technique, including dye-dilution proliferation assays. In one exemplary embodiment, B cells (such as PBMCs) can be labeled with a fluorophore (such as CFSE, etc.) cultured for a suitable period of time (such as 3-4 days) with additions of the compounds to be screened (a first cell population for the constructs to be tested, and a second population to be treated with control antibody), and fluorescence of the cells on each population assessed at the end point. As the fluorescent dye is halved as each cell division occurs the culture with the least fluorescence had the most active stimulant.

EXAMPLE 1

F(ab')2 fragments of mAb G28-8 were generated by pepsin digestion using the method of Parham (J Immunol. 1983 December; 131(6):2895-902). The pepsin digestion of G28-8 was complete, since the mAb was 160 kDa prior to digestion, and no residual 160 kDa undigested protein was detected after pepsin treatment. The digested protein was mostly 100 kDa F(ab')2 fragment as shown on the SDS PAGE analysis of nonreduced protein, with smaller digestion fragments of approximately 75 kDa and 45 kDa also present (FIG. 1).

Figure 2:
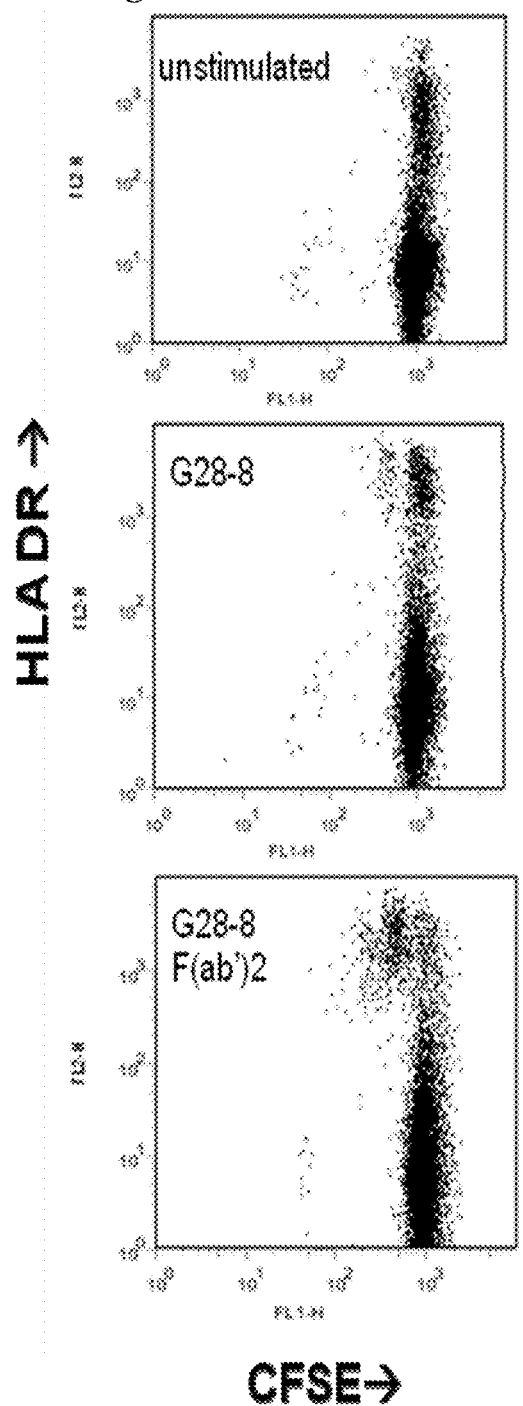

FIG. 2 shows CFSE fluorescence intensity versus MHC class II (DR) brightness of lymphocytes after incubation for 4 days with either medium alone, with mAb G28-8, or with F(ab')2 fragment of G28-8. Human peripheral blood mononuclear cells (PBMC) were isolated by centrifugation of heparanized peripheral blood, diluted 1:1 with phosphate buffered saline, over Lymphocyte Separation Medium (LSM, Cappel, Aurora, Ohio) according to manufacturer's instructions. PBMC were labeled with carboxyfluorescein diacetate, succinimidyl ester (CFSE, Molecular Probes, Oregon) according to the method of Lyons et al (J. Immunol. Methods, 171:131-137, 1994) and cultured in RPMI media supplemented with glutamine, P/S, pyruvate, and 10% FBS. Cells were cultured with no added antibody, with mAb G28-8, or with F(ab')2 fragment of G28-8 as indicated. After 4 days of culture at 37 degrees in 5% CO2, cells were stained with PE-labeled antibody to MHC class II (DR) (BD-Pharmingen 555812, lot28211) and analyzed by flow cytometry. Lymphocytes were analyzed using a FACS™ SCAN (BD, Mountain View, Calif.), and data was analyzed using FLOWJO™ software (Ashland, Oreg.). Example 1 shows that removal of the Fc region of CD180 mAb G28-8 by pepsin digestion increased its potency in stimulation of B cell proliferation, and that the increased potency was seen as an increase in the maximum effect rather than simply a shifting of the dose response curve. Example 1 also shows the sequence and binding of a recombinant scFv-Fc molecules constructed from the cloned variable regions of mAb G28-8, and their binding to human B cells.

Figure 3:
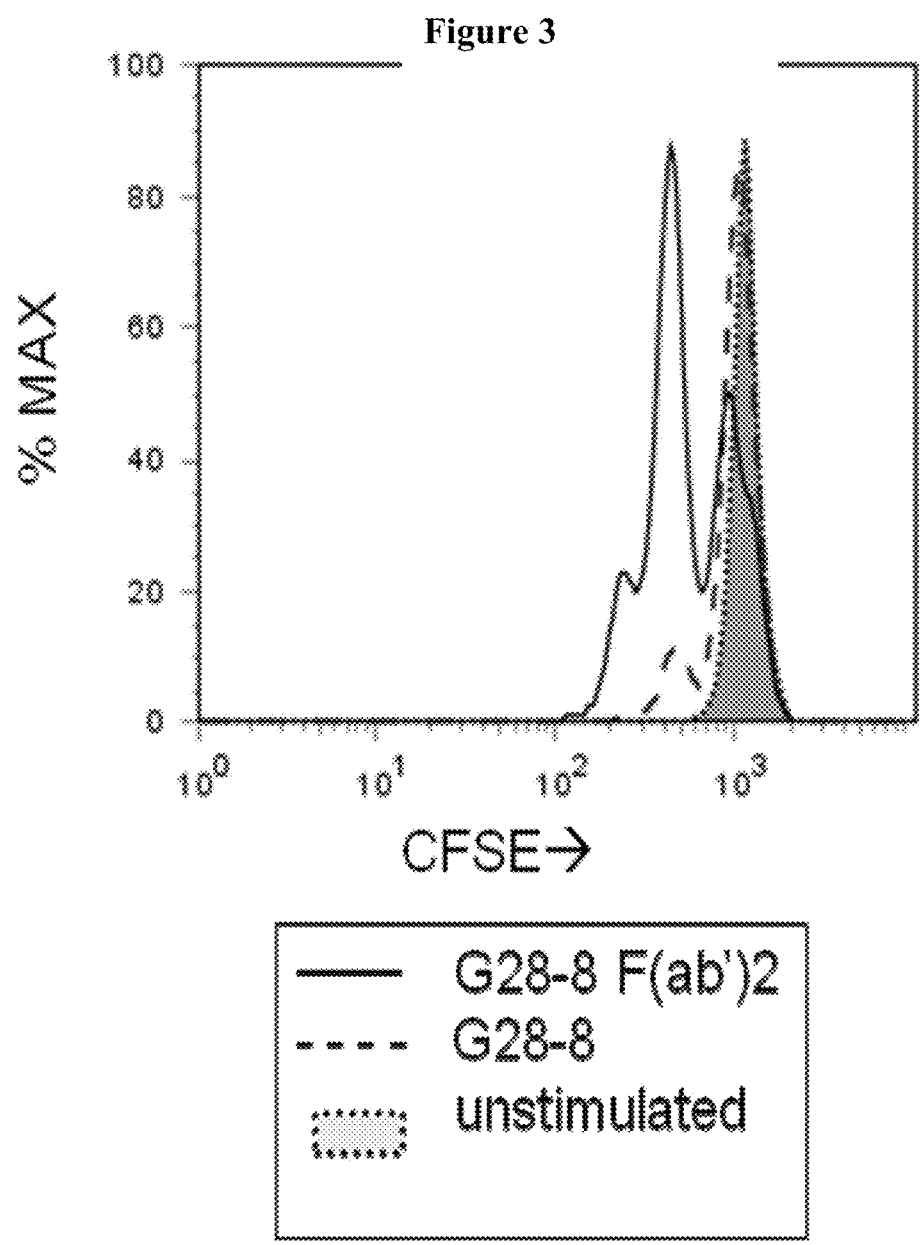
Figure 4:
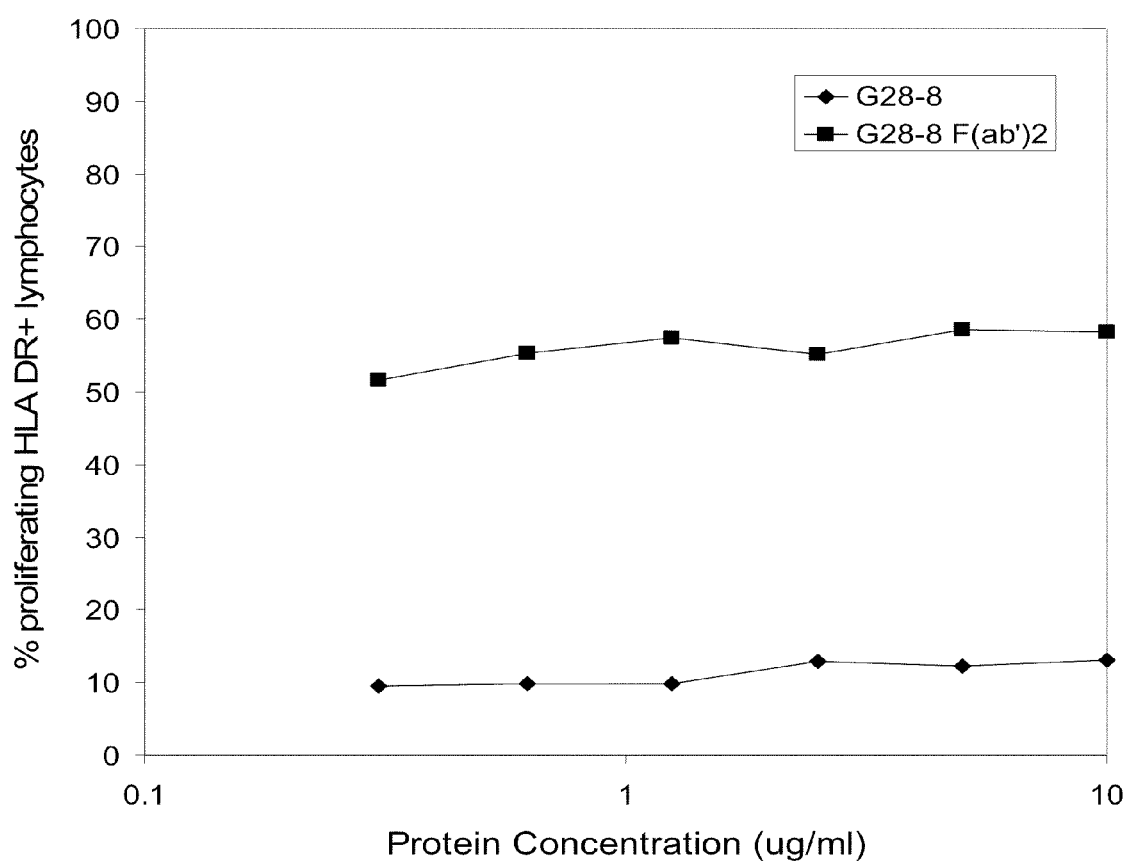

FIG. 3 shows a histogram of CFSE fluorescence intensity versus cell frequency gated on the DR positive population of blood lymphocytes, comparing the unstimulated, G28-8 stimulated, and G28-8 F(ab')2 stimulated cells. FIG. 4 shows a dose titration of G28-8 or G28-8 F(ab')2 in stimulation of B cell proliferation, graphed as the percentage of DR positive lymphocytes proliferating after 4 days culture, calculated from FLOWJO™ software (Ashland, Oreg.). FIG. 5 shows a schematic diagram of the structure of the CD180 specific scFv-Fc. FIG. 6 shows the nucleotide and predicted amino acid sequence of a scFv-Fc molecule constructed from the cloned variable regions of mAb G28-8. The Fc domain of the recombinant molecules is an altered human IgG1 Fc domain with three amino acid changes (P238S, P331S, K322S) that reduce the binding of the molecule to Fc-receptors and C1q. FIG. 7 shows a Western Blot of three different G28-8 scFvs along with CTLA4Ig, and CTLA4-Ig-4-1BB fusion proteins. Each molecule was immunoprecipitated with protein A agarose from 0.5 ml culture supernatants from COS7 cell transient transfections. COS7 cells were transiently transfected by POLYFECT™ reagent (QIAGEN) using 2.5 ug plasmid minipreps. FIG. 8 shows the binding of one of the recombinant G28-8 scFv-Fc molecules to human B cells.

To prepare an scFv, total RNA was isolated from hybridoma cells growing in log phase using QIAGEN RNEASY™ kits, including QIA shredder column purification to homogenize cell lysates, and purification over RNEASY™ minicolumns. Then cDNA was synthesized and anchor tailed, and PCR performed using an anchor-tail (CCCCCC)-complementary primer and a primer, which anneals specifically to the antisense strand of the constant region of either mouse (or rat) Ck or mouse CH 1 (or rat) for the appropriate isotype. The amplified variable region fragments were then TOPO® cloned (Invitrogen), and clones with inserts of the correct size sequenced. Consensus sequence for each variable domain are determined from sequences of at least 4 independent clones. The scFv is constructed by insertion of a variable length (gly4ser) linker (10-20 amino acids) or by PCR using overlapping primers containing a synthetic (gly4ser)3, a (gly4ser)4 or a hydrophilic linker containing a (glyser) motif at each end, with the linker domain inserted between the VL and VH regions. Constructs are fused to the human VK3 light chain signal peptide or alternatively a synthetic leader sequence derived from the sequences of several different leaders, with a Kozak signal sequence included to improve expression level of the expressed fusion proteins. Small cassettes were designed which incorporated a 5' restriction site, Kozak consensus sequence, and the leader peptide from the human VK3 germline sequence which includes an in frame Age I site at the end of the leader peptide, just upstream of the framework region for the light chain variable domain. Overlapping, partially complementary oligonucleotides were used in PCR extension reactions to create these short cassettes. PCR products of the correct size were isolated by gel electrophoresis and cloned into the pCR®-2.1 TOPO® (Invitrogen) vector.

PCR reactions were performed on the TOPO® cloned DNA using a 30 cycle program with the following profile: 94 C, 30 sec; 55 C, 30-60 sec; 68 C, 30-60 sec, followed by a final extension at 72 C for 8 minutes. PCR products were gel purified and fragments recovered using a QIAQUICK™ gel extraction kit (QIAGEN, Valencia, Calif.). Fragments were subcloned into Puc derived vectors for creating fusion genes and assembly of the scFv-Fc construct.

Usually, a VH was subcloned into a particular vector with the leader peptide cassette as a three way ligation, positive clones identified by restriction digestion, and these clones recut with the appropriate enzymes for inserting linker and VL domains together as a second three-way ligation. Fragments were mixed together in the appropriate ratios to optimize three-way ligation reactions.

Fragments were diluted 1:50 and 1 microliter used for overlap extension PCR reactions when linkers were attached in this manner instead of by multi-fragment ligation. Diluted overlapping PCR products were added to standard PCR reactions without additional primers and run for 2 cycles. Cycling was then paused, and the flanking VL 5' and VH 3' primers were added. Cycling was resumed and allowed to complete the remainder of the 30 cycle program. The temperature profile was 94 C, 60 sec; 55 C, 60 sec; and 68 C, 60 sec for 30 cycles. Human Fc domains (hinge, CH2, and CH3 domains) were isolated from blood (human and macaque) or splenic (mouse) RNA. Sequences were altered using overlap extension PCR to introduce mutations at residues implicated in mediating ADCC and CDC effector functions.

Initial expression studies were performed by transient transfection of COS cells, using POLYFECT™ (QIAGEN, Valencia, Calif.) transfection reagent according to manufacturer's instructions. Culture supernatants were harvested at 72 hours posttransfection and screened for binding to the Ramos, Bjab, or T51 B cell lymphoma lines which expresses high levels of varying levels of human CD180. Constructs were then transfected into CHO DG44 cells to create stable cell lines as described previously.

Stable production of the –Ig fusion protein was achieved by electroporation of a selectable, amplifiable plasmid, pDG, containing the RNase-Ig cDNA under the control of the CMV promoter, into Chinese Hamster Ovary (CHO) cells. The pDG vector is a modified version of pcDNA3 encoding the DHFR selectable marker with an attenuated promoter to increase selection pressure for the plasmid. Plasmid DNA was prepared using Qiagen maxiprep kits, and purified plasmid was linearized at a unique AscI site prior to phenol extraction and ethanol precipitation. Salmon sperm DNA (Sigma-Aldrich, St. Louis, Mo.) was added as carrier DNA, and 100 µg each of plasmid and carrier DNA was used to transfect $10^7$ CHO DG44 cells by electroporation. Cells were grown to logarithmic phase in EX-CELL® 302 media (JRH Biosciences) containing glutamine (4 mM), pyruvate, recombinant insulin, penicillin-streptomycin, and 2×DMEM non-essential amino acids (all from Life Technologies, Gaithersburg, Md.), hereafter referred to as "EX-CELL® 302 complete" media. Media for untransfected cells also contained HT (diluted from a 100× solution of hypoxanthine and thymidine) (Invitrogen/Life Technologies). Media for transfections under selection contained varying levels of methotrexate (SigmaAldrich) as selective agent, ranging from 50 nM to 1 µM. Electroporations were performed at 280 volts, 950 microFarads. Transfected cells were allowed to recover overnight in non-selective media prior to selective plating in 96 well flat bottom plates (Costar) at varying serial dilutions ranging from 125 cells/well to 2000 cells/well. Culture media for cell cloning was EX-CELL® 302 complete, containing 50 nM methotrexate. Once clonal outgrowth was sufficient, serial dilutions of culture supernatants from master wells were screened for expression of –Ig fusion protein by use of an –IgG sandwich ELISA. Briefly, NUNC IMMULON™ II plates were coated overnight at 4° C. with 7.5 microgram/ml F(ab'2) goat anti-mouse IgG (KPL Labs, Gaithersburg, Md.) in PBS. Plates were blocked in PBS/3% BSA, and serial dilutions of culture supernatants incubated at room temperature for 2-3 hours. Plates were washed three times in PBS/0.05% Tween 20, and incubated with horseradish peroxidase conjugated F(ab'2) goat anti-human IgG (SouthernBiotechnologies), each at 1:3000 in PBS/1.0% BSA, for 1-2 hours at room temperature. Plates were washed four times in PBS/0.05% Tween 20, and binding detected with SUREBLUE RESERVE™, TMB substrate (KPL Labs, Gaithersburg, Md.). Reactions were stopped by addition of equal volume of 1N HCl, and plates read at 450 nM. The clones with the highest production of the fusion protein were expanded into T25 and then T75 flasks to provide adequate numbers of cells for freezing and for scaling up production of the fusion protein. Production levels were further increased in cultures from the four best clones by progressive amplification in methotrexate containing culture media. At each successive passage of cells, the EX-CELL® 302 complete media contained an increased concentration of methotrexate, such that only the cells that amplified the DHFR plasmid could survive. The production level of the top four unamplified master wells from the G28-8 scFvIg CHO transfectants ranged from 30-50 micrograms/ml culture.

Supernatants were collected from CHO cells expressing the G28-8 scFvIg filtered through 0.2 µm PES express filters (Nalgene, Rochester, N.Y.) and were passed over a Protein A-agarose (IPA 300 crosslinked agarose) column (Repligen, Needham, Mass.). The column was washed with column wash buffer (90 mM Tris-Base, 150 mM NaCl, 0.05% sodium azide, pH 8.7) and bound protein was eluted using 0.1 M citrate buffer, pH 3.4. Fractions were collected into 1M bicarbonate buffer and protein concentration was determined at 280 nM using a NANODROP™ (Wilmington Del.) microsample spectrophotometer, and blank determination using 0.1 M citrate buffer, pH 3.4 with 100 ul 1M bicarbonate buffer.

EXAMPLE 2

While current anti-human CD180 antibodies (prior to the present invention) are mouse IgG1 and bind fairly strongly to human Fc receptors, generating a mixed signal to bound B cells, the rat IgG2a anti-mouse CD180 antibody used in Example 2 has very low affinity for mouse Fc receptors, thus making it a natural mimetic for the non-FcR binding constructs disclosed in the present application.

Materials and Methods

Mice

WT (C57BL/6), CD40 KO, B cell-deficient (μMT), and T cell-deficient (TCRβ/δ KO, TCR KO) mice were from Jackson Laboratory (Bar Harbor, Me.) and all other strains were on this background. MyD88 KO mice were gifts from K. Elkon (University of Washington, Seattle, Wash.). CD180 KO mice were a gift from C. Karp (Children's Research Foundation, Cincinnati, Ohio). All mice were sex and age matched and used at six to twelve weeks of age, except memory recall studies that utilized 60-week-old mice. All injections and immunizations were intraperitoneal with a fixed volume of 200 μl in PBS. The University of Washington Institutional Animal Care and Use Committee approved all animal work.

Cell Preparation and Culture

Spleens were processed by LIBERASE™ (Roche, Indianapolis, Ind.) digestion for DCs or mechanical disruption. Erythrocytes were depleted by Gey's lysis for total splenocyte preparations. B cells or DCs were isolated by three rounds of enrichment (STEM CELL technologies, Vancouver, BC, Canada) and purity exceeded 99% without expression of activation markers (CD69 or CD86) after 24 hours in unstimulated cultures.

Total splenocytes or purified cells were cultured in complete medium (RPMI-1640 supplemented with 10% fetal calf serum [Hyclone, Logan, Utah], 4 mM glutamine, 1 mM Na pyruvate, 1× Non-Essential Amino Acids, 100 IU/ml penicillin-streptomycin [Invitrogen, Carlsbad, Calif.], and 50 uM 2-mercaptoethanol [Sigma-Aldrich, St. Louis, Mo.]) in the presence of stimuli at a final cell density of $1\times10^6$/mL for 64 hours at 37° C.

ELISA Measurement of Serum Antibody and In Vitro Cytokine Production

Sera were obtained after injection of mice with mAbs and/or TLR agonists. Polystyrene plates were coated with donkey anti-mouse IgG, or goat anti-mouse IgM $F(ab')_2$ (Jackson ImmunoResearch, West Grove, Pa.). After blocking with 4% nonfat dry milk in PBS-Tween, serial dilutions of serum were added. Abs were detected with isotype-specific HRP conjugates (anti-IgG1, anti-IgG2b, and anti-IgG3 from ICL, Newberg, Oreg.; anti-IgM and anti-IgG2c from Southern Biotech, Birmingham, Ala.) and absorbance was compared with standard curves generated from mouse monoclonal standards (IgG3 from BioLegend, San Diego, Calif.; IgM from Jackson ImmunoResearch; IgG2c from Southern Biotech; IgG1 and IgG2b standards were purified in our laboratory) for absolute quantitation. No cross-reactions between standards for the IgG subclasses, IgM, or the injected Rat IgG2a mAbs were observed. Antigen specific antibody from 4-hydroxy-3-nitro-phenacetyl (NP) conjugated LPS, NP-Ficoll, or NP-chicken gamma globulin (CgG) was captured with NP-BSA coated plates (all NP reagents from BioSearch Technologies, Inc., Novato, Calif.).

IL-6, IL-10, and TNF-α concentrations in 24-hour supernatants from cultures of purified cells were measured by ELISA (DuoSets from R&D Systems, Minneapolis, Minn.) per the manufacturer's instructions.

Analysis of Lymphocyte Subsets and Proliferation

Flow cytometry analyses were performed on either a standard FACS™ SCAN or FACSCanto (Becton Dickinson, Franklin Lakes, N.J.). Minimums of 30,000 cells of the final gated population were used for all analyses. Data analysis was performed with FLOWJO™ (Tree Star, Ashland, Oreg.) software. Staining was performed for: CD3 and CD24 (Becton Dickinson clones 145-2c11 and M1/69); CD4, CD8β, CD19, CD21, and CD23 (BioLegend clones RM4-5, YTS156.7.7, 6D5, 7E9, and B3B4); CD5, CD45R/B220, and CD86 (Clones 53-7.3, RA3-6B2, and GL1 from eBioscience, San Diego, Calif.). Mouse anti-rat IgG secondary antibody was from Jackson ImmunoResearch.

CFSE (Invitrogen) labeling of cells was performed with a final concentration of 0.8 μM CFSE and $1.6\times10^7$ cells/ml in 37° C. PBS for four minutes. Proliferation Index was calculated by dividing the MFI for gated live singlet unstimulated B cells by the MFI of equivalently gated cells from the stimulated sample. This measurement simultaneously captures both percent proliferating cells and the average number of divisions per cell. A Proliferation Index of 1 indicates equivalence to unstimulated culture.

Synergy Determinations and Calculation of the Combination Index

The Combination Index (CI), a quantitative definition of synergy or antagonism, was calculated by the method of Chou and Talalay[21] through the use of CalcuSyn software (Biosoft, Cambridge, United Kingdom). As the CI method is based on the median effect principle of the mass action law, it is mechanism-independent.

Other Antibodies and Reagents

The anti-CD180 (RP/14) hybridoma was a gift from K. Miyake (University of Tokyo, Tokyo, Japan) and the rat IgG2a isotype control (9D6) hybridoma was a gift from R. Mittler (Emory University, Atlanta, Ga.). To ensure equivalence these mAb were sequentially purified on the same protein G column and routinely bioassayed both alone and in combination with polymyxin B sulfate. LPS (L2143) was from Sigma-Aldrich. Synthetic TLR agonists $Pam_2CSK_4$, $Pam_3CSK_4$, CL097, and CpG ODN1826 were from InvivoGen (San Diego, Calif.).

Statistical Analyses

Raw data of experimental groups were analyzed either by one-way ANOVA followed by Bonferroni's Multiple Comparison Test (GraphPadPrism software, version 4.0a for Macintosh, San Diego, Calif.) or by two-tailed, type two Student's t-test. Columnar data are represented as mean±standard error (SEM). A value of $p<0.05$ was considered to be statistically significant and assigned *, while $p<0.01$ and $p<0.001$ were assigned  and *, respectively.

Results

Anti-CD180 Injection Induces Polyclonal Ig Production of Multiple Isotypes

Because CD180 KO mice have low serum concentrations of IgG3[11], we examined Ig concentrations of WT mice at 3, 7, 10, and 14 days after injection with either anti-CD180 or isotype-matched control mAb (the anti-CD180 antibody is an agonistic rat IgG2a that was not expected to deplete target cells or bind significantly to FcγRIIb). At no point did the anti-CD180-injected mice show any evidence of distress, unlike TLR4 agonists which rapidly induce septic shock.

Anti-CD180 alone increased serum Ig concentration of nearly every isotype and subclass by day 3, with consistently rapid and dramatic increases for IgG1, IgG2c, and IgG3 (12, 9.5, and 56-fold increase at day 10, respectively), while changes in serum concentration of IgM were modest and IgG2b varied with an average of 1.5-fold reductions (FIG. 9A and data not shown). Semi-quantitative immunoblots for IgA and IgE from day 10 bleeds indicate that IgA concentrations were equivalent in control and anti-CD180 treated mice, while IgE concentrations increased roughly 10-fold (data not shown).

We examined whether rapid production of IgM and IgG1 after CD180 stimulation was due to reactivation of memory B cells. WT mice were immunized with NP-CgG in alum and rested for 50 weeks before injection of recall stimuli. While recall Ag administration without adjuvant produced robust NP-specific IgG1, neither anti-CD180 nor inflammatory stimuli (LPS plus anti-CD40) induced significant recall compared to unconjugated CgG (FIG. 9B). Addition of anti-CD180 stimulation with Ag did not significantly impact recall IgG1 responses.

Figure 9C:
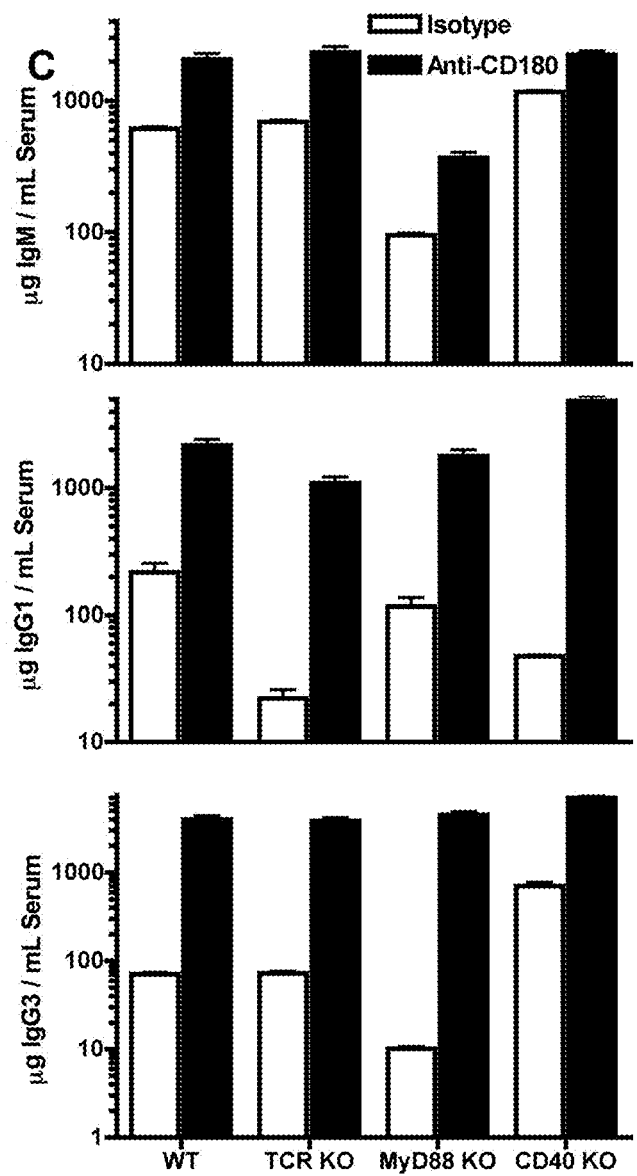

Anti-CD180-induced Ig production required neither T cells, CD40 signal support, nor TLR signaling as the increase in IgG concentrations still occurred after injection of TCR KO, CD40 KO, and MyD88 KO mice (FIG. 9C). IgM production was largely bypassed and IgG production was strikingly delayed in TCR KO mice, indicating a supportive role for T cells despite dispensability for the overall anti-CD180-induced Ig effect (FIG. 10).

To assess whether anti-CD180-induced Ig is polyclonal or an exuberant Ag-specific response, we examined both the effect of co-administration of anti-CD180 with model T cell-independent (TI) antigens as well as Ig produced against the rat IgG2a anti-CD180 mAb itself (FIG. 11). Ag-specific antibody was reduced or unchanged for all isotypes with both T cell-independent type 1 (TI-1, intrinsic B cell activating Ag, NP-LPS) and type 2 (TI-2, polyvalent Ag, NP-Ficoll). Anti-rat Ig was generated against the anti-CD180 mAb but is not more than 15% of the total IgM produced and has substantially different kinetics, with Ag-specific IgM requiring 7 days to peak while total IgM is near maximal by day 3. Class-switched anti-rat Ig was predominately IgG2c and was not produced against control mAb. T cell-deficient mice also produced IgM specific for anti-CD180, but not class-switched Ig of any subclass. Auto-reactive antibody, as determined by antinuclear antibody immunoflourescence, did not increase after anti-CD180 injection (data not shown).

Anti-CD180 Injection Expands Splenic B Cells

Three days after injection the spleens of anti-CD180-treated mice were enlarged nearly 3-fold compared to control mice (data not shown). Absolute splenic mononuclear cell numbers increased approximately 2.5-fold from controls (FIG. 12A, B). B cells (CD19$^+$) contributed the majority of the change by expanding 7, 9, and 2.5-fold in transitional 1 (T1), transitional 2 (T2), and follicular (FO) subsets respectively, while the marginal zone (MZ) B cell subset did not change significantly (FIG. 12A). This selective expansion is not predicted by CD180 expression as A) T1 and T2 B cells show equivalent expression with the FO subset but much more accumulation post injection, and B) both CD5$^+$ B cells and a subset of MZ B cells (42%) express CD180 but neither expanded following injection (FIG. 12A, C, and data not shown). Furthermore, T cell numbers also expanded significantly (FIG. 12A), despite their lack of CD180 expression, indicating an indirect effect of anti-CD180 on T cell functions in vivo.

This lymphoid cell expansion after anti-CD180 injection was transient, as cell numbers were lower at day 7 and essentially normal by day 14. The single exception was CD8$^+$ T cells, which remained expanded through day 14. The kinetics of cell expansion paralleled binding of the anti-CD180 antibody, as determined by anti-rat IgG staining ex vivo, which demonstrated maximum binding at day 3, minimal binding at day 7, and undetectable binding on day 14 (data not shown). Expansion of B cells was still evident in TCR KO mice (FIG. 12B) and showed equivalent kinetics (data not shown), indicating that T cells are not required for either expansion or contraction B cell populations in vivo following anti-CD180 injection. However, T cell expansion requires B cells, since T cells did not expand in B cell-deficient mice after anti-CD180 treatment (FIG. 12B).

Combinations of TLR and CD180 Signals Reduce B Cell Differentiation and Enhance Proliferation Due to the known interaction between CD180 and TLR4, we compared Ig production induced by anti-CD180 alone to co-injection with various TLR ligands. Combinations of anti-CD180 and LPS did not augment but instead resulted in decreased or unchanged Ig production (FIG. 13A) resulting in serum concentrations intermediate to anti-CD180 or LPS alone. This effect was also observed with Pam$_3$CSK$_4$ (TLR2:1) and CpG (TLR9), indicating a general effect of TLR signals rather than a specific interaction between CD180 and TLR4.

We also injected anti-CD180 in combination with TLR ligands (LPS or CpG) to determine whether these combinations changed how splenic lymphocytes expanded. Compared with anti-CD180 injection alone, mice injected with anti-CD180/TLR agonist combinations showed roughly equivalent B cell expansion (3.5 fold) but had reduced expansion of T cells (FIG. 13B). Despite a lack of MZ B cell expansion with anti-CD180 alone, combinations of CD180 and TLR signals increased splenic MZ B cell populations. As splenic lymphocyte analysis conflates proliferation, apoptosis, selection alteration, and tissue homing for a qualitative result we are unable to quantitatively assess the effect of CD180/TLR combination stimulation on B cell proliferation in isolation—leading us to examine the effects of CD180/TLR stimulant combinations in defined in vitro experiments.

As CD180 KO B cells have diminished proliferative responses to LPS[22], we examined possible reciprocal dependence of CD180 signals on TLR2 and TLR4. In WT splenocyte cultures the combination of CD180 and TLR4 stimulation augmented B cell proliferation compared to either stimulus alone, increasing both the percentage of B cells proliferating and the average number of cycles (FIG. 13C). Deficiency of TLR2 and TLR4 had no effect upon proliferation of B cells in response to anti-CD180, and as expected there was no LPS response. Similar results were obtained for MyD88 KO B cells (data not shown). Thus, CD180 and TLR4 provide distinct, non-redundant, and mutually reinforcing signals for B cell proliferation.

To identify the intersection of CD180 and TLR4 signaling pathways we assayed B cell proliferation with graded doses of LPS, with or without a fixed dose of anti-CD180, in splenocytes from WT, TRIF KO, and MyD88 KO mice (FIG. 13D). Despite the minimal proliferation to LPS alone, the augmentation of anti-CD180 on LPS-induced proliferation was still present in B cells from TRIF KO mice but not from MyD88 KO mice. While MyD88 is not required for CD180 signals to induce B cell proliferation, it is required to mediate the CD180 augmentation of TLR4 signals.

Anti-CD180 Synergizes with Multiple MyD88-Dependent TLR Ligands for B Cell Proliferation Since Ig production decreased after various TLR ligands were co-injected with anti-CD180, we examined the effects of TLR ligands on anti-CD180 induced proliferation in a quantitative in vitro system designed to determine the nature and magnitude of signal interactions. B cells were isolated and both anti-CD180 and TLR agonists were titrated, first separately and then together at a constant ratio, to measure interaction effects between the stimuli. In addition to TLR4 (LPS), the interactions of CD180 with TLR2:1 (Pam$_3$CSK$_4$), TLR2:6 (Pam$_2$CSK$_4$), TLR7 (CL097), TLR9 (CpG ODN1826), and BCR (anti-IgM F(ab')$_2$) were also analyzed (FIG. 14A). The proliferation of B cells to combinations of anti-CD180 mAb and TLR agonists was augmented for all combinations; however, the augmentation was most pronounced with TLR2 ligands. In contrast, antagonism was observed with BCR stimulation.

To extract quantitative information from the titration series of anti-CD180 and TLR (or BCR) interaction, the three separate titration curves were transformed into a single curve (FIG. 14B) by the Combination Index (CI) analysis method[21]. The resulting graph displays signal interaction over the entire titration range, with CI=1 indicating no interaction (mere additive effect), CI<1 indicating synergy (greater than additive effect), and CI values>1 indicating antagonism. Despite the previously reported selective relationship between CD180 and TLR4, we demonstrate synergy (CI<1) for all MyD88-dependent TLR agonist combinations with anti-CD180. Surprisingly, at very low Fractional Effects (relative doses) all combinations other than LPS revealed antagonism. While CD180 is described as a specific regulator of TLR4, our analyses show significantly greater synergy with ligands of TLR2 or TLR7. As these experiments used isolated B cells (>99% pure) the observed interactions are likely intrinsic to B cells, rather than indirect contributions from signaling in rare non-B cells.

Anti-CD180 Augments Cytokine Production by TLRs in Isolated B Cells

We next examined cytokine production from isolated B cells treated with anti-CD180 alone or in combinations with LPS or CpG (FIG. 15A). No production of IL-6, IL-10, or TNF-α was observed with anti-CD180 alone; however there was clear augmentation of cytokine production in combination with TLR ligands. Concentrations of IL-6 and IL-10 were substantially augmented even at LPS concentrations that alone resulted in no effect. Similar augmentation of cytokine production was seen in combinations with CpG and included strongly increased production of TNF-α. Isolated DCs similarly did not produce cytokines after CD180 stimulation alone (FIG. 15B). Rather than the enhancement with CD180/TLR combinations observed in isolated B cells, DCs tended to have reduced cytokine production.

Discussion

Collectively, our data indicate that CD180 signals induce an extensive and rapid burst of polyclonal proliferation and activation in naïve B cells, and proceeding to IgG production within three days. CD180 has been implicated in induction of IgG3 antibodies since constitutive serum concentrations of IgG3 in CD180 KO mice are approximately one-tenth that of WT mice[22]. Our results broaden this interpretation as anti-CD180 mAb injection caused very rapid and large increases in serum Ig concentration, with IgM, IgG1, IgG2c, and IgG3 concentrations each reaching or exceeding 1 mg/ml within 10 days of injection. IgG3 concentrations had the largest change with a >50-fold increase over basal concentrations. While robust, this response was transient as concentrations of all isotypes had peaked and begun to decline by day 14.

Injection of anti-IgD similarly induces polyclonal B cell activation and production of high serum IgG1 concentrations[23, 24], and is the closest known parallel for the effects of anti-CD180 in vivo. However, there are notable differences between the effects of anti-CD180 and anti-IgD. Anti-IgD induced polyclonal Ig was restricted to IgG1 and IgE isotypes, and required T cell help and IL-4[25, 26]. In contrast, anti-CD180 injection increased serum concentration of all isotypes and subclasses except for IgG2b and IgA, the two prototypic TGF-β induced Ig classes[27]—an effect that required neither T cells nor MyD88-dependent signaling. As B cell class-switch recombination is thought to require either T cell help or MyD88-dependent TLR/TACI signals[28], anti-CD180-induced Ig production may involve an unrecognized pathway for class-switch induction. Notably, anti-CD180 treatment is remarkable among known polyclonal activators by virtue of its profound and rapid induction of diverse Ig classes and subclasses. Additionally, while Ig production by anti-IgD required higher order clustering produced by either multiple mAbs or polyclonal sera[23, 25], a single anti-CD180 mAb induces extensive Ig production, which suggests that only ligation or dimerization is required. While our data do not support the idea of CD180 signaling via IgD, we cannot rule out the involvement of BCR components[29]. Despite the significant differences between CD180 and IgD as mediators of polyclonal activation, they still may be classified together in that both induce potent effects but have no confirmed function despite their discovery over 20 years ago.

The anti-CD180-induced Ig is polyclonal and not merely the result of an unexamined Ag-specific response. As rapid production of Ag-specific Ig can occur with either TI-1 or TI-2 antigens, and cellular debris may stimulate B cells for these responses, we examined the effect of anti-CD180 on NP-conjugated model antigens. It is unlikely that cellular debris is stimulating Ig production as Ag-specific antibody was reduced for both responses. Also, antinuclear antibody did not increase with anti-CD180 treatment (data not shown). While Ag-specific responses to independent but co-administered Ag decreased, Ig specific for the anti-CD180 mAb itself was increased, though not to more than 15% of the total IgM produced. As the bulk of the IgM and essentially all of the IgG produced by anti-CD180 treatment is neither memory nor specific for concomitantly present antigens, it is therefore likely to be polyclonal.

Injection of anti-CD180 mAb resulted in a rapid increase in splenic cellularity; three days after injection T1, T2, and FO B cell subsets expanded 7-, 9-, and 2.5-fold, respectively, whereas neither MZ nor $CD5^+$ B cells expanded. While these lymphocyte expansions conflate survival and tissue homing effects with proliferation, the magnitude is difficult to explain on the basis of enhanced survival or redistribution alone and most likely involve a component of proliferation. While T cells do not express CD180 or proliferate after anti-CD180 stimulation in vitro, their numbers are significantly increased in the spleen following anti-CD180 injection, suggesting expansion and/or recruitment of T cells to the spleen driven by other, directly activated, cells. Regardless of the mechanism, the expansion of T cells in the spleen is abrogated in B cell-deficient μMT mice, indicating that activated B cells and not other $CD180^+$ cells (DC, macrophage) are required for the effect. Increases to both B and T cell numbers were transient, approaching normal numbers by day seven after injection; only $CD8^+$ T cell numbers remained increased through day 14. The function of these persistent $CD8^+$ T cells is unknown, as anti-CD180-induced expansion and contraction of B cells were equivalent in WT and T cell-deficient mice. It is possible that the prevalence of activated B cells is mediating memory T cell reactivation without the presence of cognate antigen.

The combined injection of anti-CD180 with LPS, both inducers of polyclonal Ig, did not further increase Ig in serum, but instead resulted in a reduction of Ig levels to concentrations intermediate to those seen with either stimulus alone. A similar effect was seen with co-injection of anti-CD180 with either TLR9 or TLR2:1 ligands (CpG or $Pam_3CSK_4$). The suppression of anti-CD180 induced Ig by different TLR ligands suggests either a restraining effect of non-B cells or an intrinsic negative regulation by TLR signals of CD180 stimulated B cell differentiation upon the integration of TLR signals. Our data support a model where combinations of CD180 and TLR signals drive greater B cell proliferation at the expense of differentiation and Ig production.

Our data regarding B cell proliferation to anti-CD180 and LPS are not consistent with models suggesting CD180 functions by forming heterodimers only with TLR4 and regulating the canonical LPS signal[4]. Unlike LPS, the B cell proliferative response to anti-CD180 does not require MyD88, TRIF, or TLR4, and also TLR2 is not required. However, CD180 and TLR signals appear to be integrated through MyD88 because the combination of anti-CD180 and LPS signals augments B cell proliferation in TRIF-deficient but not MyD88-deficient B cells. Taken together, these results indicate that CD180 signals augment, but are independent from, those of TLR4. Given these findings, we hypothesized that other MyD88-dependent TLRs (e.g. TLR9, TLR7, TLR2:6, and TLR2:1) would also enhance B cell proliferation in response to CD180 ligation. Indeed, strong augmentation was evident with anti-CD180 and all TLR ligands tested. This effect may not have been detected in previous studies, which used only single concentrations of ligand combinations; saturation concentrations may have resulted in an insignificant augmentation unlike sub-maximal doses. As TLR7 and TLR9 are largely endosomal[30], and not at the cell surface where CD180 is found, our data are not consistent with a model of CD180 function involving direct interactions with TLRs to augment B cell proliferation.

Our analysis allowed the use of the mathematical transformation described by Chou and Talalay[22] to quantify synergy over broad dose ranges. Synergy is highest between anti-CD180 and the TLR2 ligands, followed by TLR7, then by TLR9, with the least synergy between CD180 and TLR4. The analysis also revealed previously unreported antagonism between anti-CD180 and all MyD88-dependent TLR ligands, excluding LPS, at very low doses. Neither of these patterns is predicted by existing models of CD180 as a selectively forming heterodimers with TLR4, regardless of whether the interaction is stimulatory or inhibitory. Regardless of whether CD180 acts as a specific TLR4 "decoy" receptor in B cells, as proposed for DCs[3], or a required co-receptor for a single B cell LPS pathway[22], the effect should impact both the MyD88 and TRIF signaling pathways for LPS and no effect would be expected for other TLRs. Thus, our findings showing that CD180 synergizes with multiple TLR ligands in a MyD88-dependent TRIF-independent manner to enhance proliferation at nearly all dose levels suggest an alternative model where independent CD180 and TLR signals converge in B cells at the level of MyD88.

While anti-CD180 stimulation of purified B cells induced proliferation, it did not induce cytokine production. However, in combination with LPS, anti-CD180 stimulation increased production of IL-10 and IL-6, but not TNF-α, while anti-CD180 plus CpG increased production of all of these cytokines. The IL-10 concentrations were high (>1,000 pg/ml), suggesting that CD180 signals could be involved in development of anti-inflammatory IL-10 secreting B cells[31]. Due to the complex effects of IL-10, which can both suppress inflammation and activate B cells[32,33], it is possible that combined CD180/TLR signaling may minimize TLR-induced inflammation while promoting select B cell functions. As with B cells, DCs failed to produce cytokines with anti-CD180 stimulation alone, however unlike B cells they did not augment TLR-induced cytokine production. A combination of evidence regarding anti-CD180 treatment—the lack of DC responsiveness, the requirement of B cells for splenic expansion, the production of high serum concentrations of Ig in both WT and T cell-deficient mice, and the proliferation of purified B cells in vitro—together suggest that CD180 stimulation is primarily mediated by, and intrinsic to, B cells.

Our study of CD180 is unique in that use of an agonistic antibody allows us to perform quantitative interaction assays over broad dose ranges and characterize acute responses as opposed to genetic deletion that results in data that is singular in both dose and kinetics. Taken together, our results suggest that CD180 stimulation plays an important role in B cell proliferation, activation, and differentiation, and that these effects are significantly modulated by integration of MyD88-dependent TLR signals. While it remains to be determined whether the rapidly induced class-switched Ig also involves somatic hypermutation, it appears to be polyclonal. Finally, because anti-CD180 treatment induces immunomodulatory effects (augmenting anti-inflammatory IL-10, blunting Ag-specific responses, and producing polyclonal Ig which may clear apoptotic debris like natural antibody) it has therapeutic potential in systemic autoimmune diseases.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

REFERENCES FOR EXAMPLE 2

1. Valentine M A, Clark E A, Shu G L, Norris N A, Ledbetter J A. Antibody to a novel 95-kDa surface glycoprotein on human B cells induces calcium mobilization and B cell activation. *J. Immunol.* 1988; 140(12):4071-4078.
2. Miyake K, Yamashita Y, Ogata M, Sudo T, Kimoto M. RP105, a novel B cell surface molecule implicated in B cell activation, is a member of the leucine-rich repeat protein family. *J. Immunol.* 1995; 154(7):3333-3340.
3. Divanovic S, Trompette A, Atabani S, et al. Negative regulation of TLR4 signaling by RP105. *Nat. Immunol.* 2005; 6(6):571-578.
4. Nagai Y, Shimazu R, Ogata H, et al. Requirement for MD-1 in cell surface expression of RP105/CD180 and B-cell responsiveness to lipopolysaccharide. *Blood* 2002; 99(5):1699-1705.
5. Groeneveld P H, Erich T, Kraal G. In vivo effects of LPS on B lymphocyte subpopulations. Migration of marginal zone-lymphocytes and IgD-blast formation in the mouse spleen. *Immunobiology* 1985; 170(5):402-411.
6. Fedele G, Celestino I, Spensieri F, et al. Lipooligosaccharide from *Bordetella pertussis* induces mature human monocyte-derived dendritic cells and drives a Th2 biased response. *Microbes Infect.* 2007; 9(7):855-863.
7. O'Neill L A, Bowie A G. The family of five: TIR-domain-containing adaptors in Toll-like receptor signaling. *Nat. Rev. Immunol.* 2007; 7(5):353-364.
8. Jin M S, Kim S E, Heo J Y, et al. Crystal structure of the TLR1-TLR2 heterodimer induced by binding of a tri-acylated lipopeptide. *Cell* 2007; 130(6):1071-1082.
9. Trinchieri G, Sher A. Cooperation of Toll-like receptor signals in innate immune defence. *Nat. Rev. Immunol.* 2007; 7(3):179-190.
10. Zhu Q, Egelston C, Vivekanandhan A, et al. Toll-like receptor ligands synergize through distinct dendritic cell pathways to induce T cell responses: implications for vaccines. *Proc. Natl. Acad. Sci. USA* 2008; 105(42):16260-16265.

11. Nagai Y, Kobayashi T, Motoi Y, et al. The Radioprotective 105/MD-1 complex links TLR2 and TLR4/MD-2 in response to microbial membranes. *J. Immunol.* 2005; 174(11):7043-7049.
12. Kim H M, Park B S, Kim J I, et al. Crystal structure of the TLR4-MD-2 complex with bound endotoxin antagonist eritoran. *Cell* 2007; 130(5):906-917.
13. Tsuneyoshi, N., Fukudome, K., Kohara, J., et al. The functional and structural properties of MD-2 required for lipopolysaccharide binding are absent in MD-1. *J. Immunol.* 2005; 174(1):340-344.
14. Harada H, Ohto U, Satow Y. Crystal structure of mouse MD-1 with endogenous phospholipid bound in its cavity. *J. Mol. Biol.* 2010; 400(4):838-846.
15. Miyake K, Yamashita Y, Hitoshi Y, Takatsu K, Kimoto M. Murine B cell proliferation and protection from apoptosis with an antibody against a 105-kD molecule: unresponsiveness of X-linked immunodeficient B cells. *J. Exp. Med.* 1994; 180(4):1217-1224.
16. Chan V W, Mecklenbrauker I, Su I, et al. The molecular mechanism of B cell activation by Toll-like receptor protein RP-105. *J. Exp. Med.* 1998; 188(1):93-101.
17. Yazawa N, Fujimoto M, Sato S, et al. CD19 regulates innate immunity by the Toll-like receptor RP105 signaling in B lymphocytes. *Blood* 2003; 102(4):1374-1380.
18. Nunez Miguel R, Wong J, Westoll J F, et al. A dimer of the Toll-like receptor 4 cytoplasmic domain provides a specific scaffold for the recruitment of signaling adaptor proteins. *PLoS One* 2007; 2(8):e788.
19. Nyman T, Stenmark P, Flodin S, Johanson I, Hammarstrom M, Nordlund P. The crystal structure of the human Toll-like receptor 10 cytoplasmic domain reveals a putative signaling dimer. *J. Biol. Chem.* 2008; 283(18):11861-11865.
20. Divanovic S, Trompette A, Petinot L K, et al. Regulation of TLR4 signaling and the host interface with pathogens and danger: the role of RP105. *J. Leukoc. Biol.* 2007; 82(2):265-271.
21. Chou T C, Talalay P. Quantitative analysis of dose-effect relationships: the combined effects of multiple drugs or enzyme inhibitors. *Adv. Enzyme Regul.* 1984; 22:27-55.
22. Ogata H, Su I, Miyake K, et al. The toll-like receptor protein RP105 regulates lipopolysaccharide signaling in B cells. *J. Exp. Med.* 2000; 192(1):23-29.
23. Goroff D K, Holmes J M, Bazin H, Nisol F, and Finkelman F. Polyclonal activation of the murine immune system by an antibody to IgD. XI. Contribution of membrane IgD cross-linking to the generation of an in vivo polyclonal antibody response. *J. Immunol.* 1991; 146(1):18-25.
24. Finkelman F, Snapper C M, Mountz J D, and Katona I M. Polyclonal activation of the murine immune system by an antibody to IgD. IX. Induction of a polyclonal IgE response. *J. Immunol.* 1987; 138(9):2826-2830.
25. Finkelman F, Scher I, Mond J J, Kung J T, and Metcalf E S. Polyclonal activation of the murine immune system by an antibody to IgD. I. Increase in cell size and DNA synthesis. *J. Immunol.* 1982; 129(2):629-637.
26. Finkelman F, Scher I, Mond J J, Kessler S, Kung J T, and Metcalf E S. Polyclonal activation of the murine immune system by an antibody to IgD. II. Generation of polyclonal antibody production and cells with surface IgG. *J. Immunol.* 1982; 129(2):638-646.
27. Park S R, Seo G Y, Choi A J, Stavnezer J, and Kim P H. Analysis of transforming growth factor-beta1-induced Ig germ-line gamma2b transcription and its implication for IgA isotype switching. *Eur. J. Immunol.* 2005; 35(3):946-956.
28. Rijkers G T, Griffionen A W, Zegers B J, and Cambier J C. Ligation of membrane immunoglobulin leads to inactivation of the signal-transducing ability of membrane immunoglobulin, CD19, CD21, and B-cell gp95. *Proc. Nat. Acad. Sci. USA.* 1990; 87(22):8766-8770.
29. He B, Santamaria R, Xu W, et al. The transmembrane activator TACI triggers immunoglobulin class switching by activating B cells throught the adaptor MyD88. *Nat. Immunol.* 2010; 11(9):836-845.
30. Eaton-Bassiri A, Dillon S B, Cunningham M, et al. Toll-like receptor 9 can be expressed at the cell surface of distinct populations of tonsils and human peripheral blood mononuclear cells. *Infect. Immun.* 2004; 72(12):7202-7211.
31. DiLillo D J, Matsushita T, Tedder T F. B10 cells and regulatory B cells balance immune responses during inflammation, autoimmunity, and cancer. *Ann. N.Y. Acad. Sci.* 2010; 1183:38-57.
32. Moore K W, de Waal Malefyt R, Coffman R L, O'Garra A. Interleukin-10 and the interleukin-10 receptor. *Annu. Rev. Immunol.* 2001; 19:683-765.
33. Rousset F, Garcia E, Defiance T, et al. Interleukin-10 is a potent growth and differentiation factor for activated human B lymphocytes. *Proc. Natl. Acad. Sci. USA* 1992; 89(5):1890-1893.

We claim:

1. An isolated anti-CD180 antibody or an antigen binding fragment thereof, comprising the complete amino acid of SEQ ID NO:2.

* * * * *

SEQUENCE LISTING

```
<160> NUMBER OF SEQ ID NOS: 10

<210> SEQ ID NO 1
<211> LENGTH: 1521
<212> TYPE: DNA
<213> ORGANISM: Artificial Sequence
<220> FEATURE:
<223> OTHER INFORMATION: G28-8 scFv-mthIgG1 -- Full-length construct

<400> SEQUENCE: 1
atggaaaccc cagcgcagct tctcttcctc ctgctactct ggctcccaga taccaccggt      60
gacatccaga tgactcagtc tccagcctcc ctatctgcat ctgtgggaga aactgtcacc     120
atcacatgtc gagcaagtga aagatttac agttatttag catggtatca gcagaaacag     180
ggaaaatctc ctcagctcct ggtctataac gcaaaaacct tagcagaagg tgtgccatca     240
aggttcagtg tcagtggatc aggcacacag ttttctctga ggatcaacag cctgcagcct     300
```

-continued

```
gaagattttg ggacttatta ctgtcaacat cattttggtt ctcctcggac gttcggtgga    360
ggcaccaaac tggaaatcaa agatctcgga ggaggtggct caggtggtgg aggatctgga    420
ggaggtggga gtggtggagg tggttctacc ggtgaggtcc agctgcaaca gtctggacct    480
gaactggtga agcctggagc ttcaatgaag atatcctgca aggcttctgg ttactcattc    540
actggctaca ccatgaactg ggtgaagcag agccatggaa agacccttga atggattgga    600
cttattaatc cttacaatgg tgttactagc tacaaccaga agttcaagga caaggccaca    660
ttaactgtag acaagtcatc cagcacagcc tacatggaac tcctcagtct gacatctgag    720
gactctgcaa tctattactg tgcaagagac tataattacg actactttga ctactggggc    780
caaggcacca ctctcacagt tcctcagatc tcgagcccaa atcttctgac aaaactcac    840 acatgtccac cgtgtccagc acctgaactc ctggggtggat cgtcagtctt cctcttcccc    900
ccaaaaccca aggacactct catgatctcc cggacccctg aggtcacgtg cgtggtggtg    960
gacgtgagcc aggaagaccc cgaggtccag ttcaactggt acgtggacgg catggaggtg   1020
cataatgcca agacaaagcc acgggaggag cagttcaaca gcacgttccg tgtggtcagc   1080
gtcctcaccg tcgtgcacca ggactggctg aacggcaagg agtacaagtg caaggtctcc   1140
aacaaagccc tcccagcctc catcgagaaa acaatctcca aaaccaaagg cagccccga    1200 gaaccacagg tgtacaccct gcccccatcc cgggaggaga tgaccaagaa ccaggtcagc   1260
ctgacctgcc tggtcaaagg cttctatccc agcgacatcg ccgtggagtg ggagagcaat   1320
gggcagccgg agaacaacta caacaccacg cctcccgtgc tggactccga cggctccttc   1380
tccctctaca gcaagctcac cgtggacaag agcaggtggc agcaggggaa cgtcttctca   1440
tgctccgtga tgcatgaggc tctgcacaac cactacacgc agaagagcct ctctctgtct   1500
ccgggtaaat gataatctag a                                              1521
```

<210> SEQ ID NO 2
<211> LENGTH: 483
<212> TYPE: PRT
<213> ORGANISM: Artificial Sequence
<220> FEATURE:
<223> OTHER INFORMATION: G28-8 scFv-mthIgG1 -- Predicted mature protein

<400> SEQUENCE: 2

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Lys Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Val
    50                  55                  60

Ser Gly Ser Gly Thr Gln Phe Ser Leu Arg Ile Asn Ser Leu Gln Pro
65                  70                  75                  80

Glu Asp Phe Gly Thr Tyr Tyr Cys Gln His His Phe Gly Ser Pro Arg
                85                  90                  95

Thr Phe Gly Gly Gly Thr Lys Leu Glu Ile Lys Asp Leu Gly Gly Gly
            100                 105                 110

Gly Ser Gly Gly Gly Gly Ser Gly Gly Gly Gly Ser Gly Gly Gly Gly
        115                 120                 125

Ser Thr Gly Glu Val Gln Leu Gln Gln Ser Gly Pro Glu Leu Val Lys
    130                 135                 140
```

```
Pro Gly Ala Ser Met Lys Ile Ser Cys Lys Ala Ser Gly Tyr Ser Phe
145                 150                 155                 160

Thr Gly Tyr Thr Met Asn Trp Val Lys Gln Ser His Gly Lys Thr Leu
            165                 170                 175

Glu Trp Ile Gly Leu Ile Asn Pro Tyr Asn Gly Val Thr Ser Tyr Asn
            180                 185                 190

Gln Lys Phe Lys Asp Lys Ala Thr Leu Thr Val Asp Lys Ser Ser Ser
        195                 200                 205

Thr Ala Tyr Met Glu Leu Leu Ser Leu Thr Ser Glu Asp Ser Ala Ile
    210                 215                 220

Tyr Tyr Cys Ala Arg Asp Tyr Asn Tyr Asp Tyr Phe Asp Tyr Trp Gly
225                 230                 235                 240

Gln Gly Thr Thr Leu Thr Val Ser Ser Asp Leu Glu Pro Lys Ser Ser
            245                 250                 255

Asp Lys Thr His Thr Cys Pro Pro Cys Pro Ala Pro Glu Leu Leu Gly
            260                 265                 270

Gly Ser Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser Gln
    290                 295                 300

Glu Asp Pro Glu Val Gln Phe Asn Trp Tyr Val Asp Gly Met Glu Val
305                 310                 315                 320

His Asn Ala Lys Thr Lys Pro Arg Glu Glu Gln Phe Asn Ser Thr Phe
                325                 330                 335

Arg Val Val Ser Val Leu Thr Val Val His Gln Asp Trp Leu Asn Gly
            340                 345                 350

Lys Glu Tyr Lys Cys Lys Val Ser Asn Lys Ala Leu Pro Ala Ser Ile
        355                 360                 365

Glu Lys Thr Ile Ser Lys Thr Lys Gly Gln Pro Arg Glu Pro Gln Val
    370                 375                 380

Tyr Thr Leu Pro Pro Ser Arg Glu Glu Met Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Asn Thr Thr Pro Pro
            420                 425                 430

Val Leu Asp Ser Asp Gly Ser Phe Ser Leu Tyr Ser Lys Leu Thr Val
        435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys

<210> SEQ ID NO 3
<211> LENGTH: 503
<212> TYPE: PRT
<213> ORGANISM: Artificial Sequence
<220> FEATURE:
<223> OTHER INFORMATION: G28-8 scFv-mthIgG1 -- Predicted full-length
      protein with signal peptide

<400> SEQUENCE: 3

Met Glu Thr Pro Ala Gln Leu Leu Phe Leu Leu Leu Leu Trp Leu Pro
1               5                   10                  15
```

```
Asp Thr Thr Gly Asp Ile Gln Met Thr Gln Ser Pro Ala Ser Leu Ser
            20                  25                  30

Ala Ser Val Gly Glu Thr Val Thr Ile Thr Cys Arg Ala Ser Glu Lys
        35                  40                  45

Ile Tyr Ser Tyr Leu Ala Trp Tyr Gln Gln Lys Gln Gly Lys Ser Pro
 50                  55                  60

Gln Leu Leu Val Tyr Asn Ala Lys Thr Leu Ala Glu Gly Val Pro Ser
 65                  70                  75                  80

Arg Phe Ser Val Ser Gly Ser Gly Thr Gln Phe Ser Leu Arg Ile Asn
            85                  90                  95

Ser Leu Gln Pro Glu Asp Phe Gly Thr Tyr Tyr Cys Gln His His Phe
            100                 105                 110

Gly Ser Pro Arg Thr Phe Gly Gly Gly Thr Lys Leu Glu Ile Lys Asp
            115                 120                 125

Leu Gly Gly Gly Gly Ser Gly Gly Gly Ser Gly Gly Gly Gly Ser
130                 135                 140

Gly Gly Gly Gly Ser Thr Gly Glu Val Gln Leu Gln Gln Ser Gly Pro
145                 150                 155                 160

Glu Leu Val Lys Pro Gly Ala Ser Met Lys Ile Ser Cys Lys Ala Ser
                165                 170                 175

Gly Tyr Ser Phe Thr Gly Tyr Thr Met Asn Trp Val Lys Gln Ser His
            180                 185                 190

Gly Lys Thr Leu Glu Trp Ile Gly Leu Ile Asn Pro Tyr Asn Gly Val
            195                 200                 205

Thr Ser Tyr Asn Gln Lys Phe Lys Asp Lys Ala Thr Leu Thr Val Asp
    210                 215                 220

Lys Ser Ser Ser Thr Ala Tyr Met Glu Leu Leu Ser Leu Thr Ser Glu
225                 230                 235                 240

Asp Ser Ala Ile Tyr Tyr Cys Ala Arg Asp Tyr Asn Tyr Asp Tyr Phe
                245                 250                 255

Asp Tyr Trp Gly Gln Gly Thr Thr Leu Thr Val Ser Ser Asp Leu Glu
            260                 265                 270

Pro Lys Ser Ser Asp Lys Thr His Thr Cys Pro Pro Cys Pro Ala Pro
        275                 280                 285

Glu Leu Leu Gly Gly Ser Ser Val Phe Leu Phe Pro Pro Lys Pro Lys
        290                 295                 300

Asp Thr Leu Met Ile Ser Arg Thr Pro Glu Val Thr Cys Val Val Val
305                 310                 315                 320

Asp Val Ser Gln Glu Asp Pro Glu Val Gln Phe Asn Trp Tyr Val Asp
                325                 330                 335

Gly Met Glu Val His Asn Ala Lys Thr Lys Pro Arg Glu Glu Gln Phe
            340                 345                 350

Asn Ser Thr Phe Arg Val Val Ser Val Leu Thr Val Val His Gln Asp
            355                 360                 365

Trp Leu Asn Gly Lys Glu Tyr Lys Cys Lys Val Ser Asn Lys Ala Leu
    370                 375                 380

Pro Ala Ser Ile Glu Lys Thr Ile Ser Lys Thr Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Thr Cys Leu Val Lys Gly Phe Tyr Pro Ser Asp
            420                 425                 430
```

```
Ile Ala Val Glu Trp Glu Ser Asn Gly Gln Pro Glu Asn Asn Tyr Asn
            435                 440                 445

Thr Thr Pro Pro Val Leu Asp Ser Asp Gly Ser Phe Ser Leu Tyr Ser
        450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
            500

<210> SEQ ID NO 4
<211> LENGTH: 736
<212> TYPE: DNA
<213> ORGANISM: Artificial Sequence
<220> FEATURE:
<223> OTHER INFORMATION: Nucleotide sequence of SCC-Hinge-WT IgG1
      cassette

<400> SEQUENCE: 4
agatctcgag cccaaatctt ctgacaaaac tcacacatgt ccaccgtgcc cagcacctga    60
actcctgggg ggaccgtcag tcttcctctt ccccccaaaa cccaaggaca ccctcatgat   120
ctcccggacc cctgaggtca catgcgtggt ggtggacgtg agccacgaag accctgaggt   180
caagttcaac tggtacgtgg acggcgtgga ggtgcataat gccaagacaa agccgcggga   240
ggagcagtac aacagcacgt accgtgtggt cagcgtcctc accgtcctgc accaggactg   300
gctgaatggc aaggagtaca gtgcaaggt ctccaacaaa gccctcccag cccccatcga   360
gaaaaccatc tccaaagcca agggcagcc cgagaacca caggtgtaca ccctgccccc   420
atcccgggat gagctgacca gaaccaggt cagcctgacc tgcctggtca aaggcttcta   480
tcccagcgac atcgccgtgg agtgggagag caatgggcag ccggagaaca actacaagac   540
cacgcctccc gtgctggact ccgacggctc cttcttcctc tacagcaagc tcaccgtgga   600
caagagcagg tggcagcagg ggaacgtctt ctcatgctcc gtgatgcatg aggctctgca   660
caaccactac acgcagaaga gcctctctct gtctccgggt aaatgataat ctagaaacag   720
gcctaagggc gaattc                                                   736

<210> SEQ ID NO 5
<211> LENGTH: 234
<212> TYPE: PRT
<213> ORGANISM: Artificial Sequence
<220> FEATURE:
<223> OTHER INFORMATION: Predicted human IgG1 Fc amino acid sequence
      without insertions/markers

<400> SEQUENCE: 5

Asp Leu Glu Pro Lys Ser Ser Asp Lys Thr His Thr Cys Pro Pro Cys
1               5                   10                  15

Pro Ala Pro Glu Leu Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
```

85                  90                  95
His Gln Asp Trp Leu Asn Gly Lys Glu Tyr Lys Cys Lys Val Ser Asn
                100                 105                 110
Lys Ala Leu Pro Ala Pro Ile Glu Lys Thr Ile Ser Lys Ala Lys Gly
                115                 120                 125
Gln Pro Arg Glu Pro Gln Val Tyr Thr Leu Pro Pro Ser Arg Asp Glu
            130                 135                 140
Leu Thr Lys Asn Gln Val Ser Leu Thr Cys Leu Val Lys Gly Phe Tyr
145                 150                 155                 160
Pro Ser Asp Ile Ala Val Glu Trp Glu Ser Asn Gly Gln Pro Glu Asn
                165                 170                 175
Asn Tyr Lys Thr Thr Pro Pro Val Leu Asp Ser Asp Gly Ser Phe Phe
                180                 185                 190
Leu Tyr Ser Lys Leu Thr Val Asp Lys Ser Arg Trp Gln Gln Gly Asn
                195                 200                 205
Val Phe Ser Cys Ser Val Met His Glu Ala Leu His Asn His Tyr Thr
            210                 215                 220
Gln Lys Ser Leu Ser Leu Ser Pro Gly Lys
225                 230

<210> SEQ ID NO 6
<211> LENGTH: 234
<212> TYPE: PRT
<213> ORGANISM: Artificial Sequence
<220> FEATURE:
<223> OTHER INFORMATION: Human IgG1 squence with SCC hinge, wild-type
      CH2-CH3

<400> SEQUENCE: 6

Asp Leu Glu Pro Lys Ser Ser Asp Lys Thr His Thr Cys Pro Pro Cys
1               5                   10                  15
Pro Ala Pro Glu Leu Leu Gly Gly Pro Ser Val Phe Leu Phe Pro Pro
            20                  25                  30
Lys Pro Lys Asp Thr Leu Met Ile Ser Arg Thr Pro Glu Val Thr Cys
        35                  40                  45
Val Val Val Asp Val Ser His Glu Asp Pro Glu Val Lys Phe Asn Trp
    50                  55                  60
Tyr Val Asp Gly Val Glu Val His Asn Ala Lys Thr Lys Pro Arg Glu
65                  70                  75                  80
Glu Gln Tyr Asn Ser Thr Tyr Arg Val Val Ser Val Leu Thr Val Leu
                85                  90                  95
His Gln Asp Trp Leu Asn Gly Lys Glu Tyr Lys Cys Lys Val Ser Asn
                100                 105                 110
Lys Ala Leu Pro Ala Pro Ile Glu Lys Thr Ile Ser Lys Ala Lys Gly
                115                 120                 125
Gln Pro Arg Glu Pro Gln Val Tyr Thr Leu Pro Pro Ser Arg Asp Glu
            130                 135                 140
Leu Thr Lys Asn Gln Val Ser Leu Thr Cys Leu Val Lys Gly Phe Tyr
145                 150                 155                 160
Pro Ser Asp Ile Ala Val Glu Trp Glu Ser Asn Gly Gln Pro Glu Asn
                165                 170                 175
Asn Tyr Lys Thr Thr Pro Pro Val Leu Asp Ser Asp Gly Ser Phe Phe
                180                 185                 190
Leu Tyr Ser Lys Leu Thr Val Asp Lys Ser Arg Trp Gln Gln Gly Asn
                195                 200                 205

```
Val Phe Ser Cys Ser Val Met His Glu Ala Leu His Asn His Tyr Thr
        210                 215                 220

Gln Lys Ser Leu Ser Leu Ser Pro Gly Lys
225                 230
```

<210> SEQ ID NO 7
<211> LENGTH: 687
<212> TYPE: DNA
<213> ORGANISM: Artificial Sequence
<220> FEATURE:
<223> OTHER INFORMATION: Nucleotide sequence of human IgG4 hinge-CH2-CH3

<400> SEQUENCE: 7

```
gagtccaaat atggtccccc gtgcccatca tgcccagcac ctgagttcct ggggggacca      60
tcagtcttcc tgttcccccc aaaacccaag gacactctca tgatctcccg gacccctgag     120
gtcacgtgcg tggtggtgga cgtgagccag gaagacccccg aggtccagtt caactggtac    180
gtggatggcg tggaggtgca taatgccaag acaaagccgc gggaggagca gttcaacagc     240
acgtaccgtg tggtcagcgt cctcaccgtc gtgcaccagg actggctgaa cggcaaggag     300
tacaagtgca aggtctccaa caaaggcctc ccgtcctcca tcgagaaaac catctccaaa    360
gccaaagggc agccccgaga gccacaggtg tacaccctgc ccccatccca ggaggagatg    420
accaagaacc aggtcagcct gacctgcctg gtcaaaggct tctacccag cgacatcgcc     480
gtggagtggg agagcaatgg gcagccggag aacaactaca agaccacgcc tcccgtgctg    540
gactccgacg gctccttctt cctctacagc aggctaaccg tggacaagag caggtggcag    600
gaggggaatg tcttctcatg ctccgtgatg catgaggctc tgcacaacca ctacacgcag    660
aagagcctct ccctgtctct gggtaaa                                        687
```

<210> SEQ ID NO 8
<211> LENGTH: 229
<212> TYPE: PRT
<213> ORGANISM: Artificial Sequence
<220> FEATURE:
<223> OTHER INFORMATION: Predicted amino acid sequence of wild-type
      human IgG4-hinge-CH2-CH3-1 allotype

<400> SEQUENCE: 8

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Phe Asn Ser
65                  70                  75                  80

Thr Tyr Arg Val Val Ser Val Leu Thr Val Val His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
```

```
                        145                 150                 155                 160
                    Val Glu Trp Glu Ser Asn Gly Gln Pro Glu Asn Asn Tyr Lys Thr Thr
                                        165                 170                 175

Pro Pro Val Leu Asp Ser Asp Gly Ser Phe Phe Leu Tyr Ser Arg Leu
                                    180                 185                 190

Thr Val Asp Lys Ser Arg Trp Gln Glu Gly Asn Val Phe Ser Cys Ser
                                195                 200                 205

Val Met His Glu Ala Leu His Asn His Tyr Thr Gln Lys Ser Leu Ser
                            210                 215                 220

Leu Ser Leu Gly Lys
                    225

<210> SEQ ID NO 9
                    <211> LENGTH: 5
                    <212> TYPE: PRT
                    <213> ORGANISM: Artificial Sequence
                    <220> FEATURE:
                    <223> OTHER INFORMATION: Synthetic

<400> SEQUENCE: 9

Lys Leu Glu Ile Lys
                    1               5

<210> SEQ ID NO 10
                    <211> LENGTH: 5
                    <212> TYPE: PRT
                    <213> ORGANISM: Artificial Sequence
                    <220> FEATURE:
                    <223> OTHER INFORMATION: Synthetic

<400> SEQUENCE: 10

Leu Thr Val Ser Ser
                    1               5
```